(12) United States Patent
Frederick et al.

(10) Patent No.: US 8,900,320 B2
(45) Date of Patent: Dec. 2, 2014

(54) METHODS AND APPARATUS FOR FAI SURGERIES

(75) Inventors: Phillip Frederick, Memphis, TN (US); Kevin Belew, Hernando, MS (US); Lauren Jasper, Memphis, TN (US); James Gatewood, Memphis, TN (US); Luke Gibson, Southhaven, MS (US); John Masonis, Charlotte, NC (US); Michael Cooper, Nesbit, MS (US); David C. Kelman, Collierville, TN (US)

(73) Assignee: Smith & Nephew, Inc, Cordova, TN (US)

( * ) Notice: Subject to any disclaimer, the term of this patent is extended or adjusted under 35 U.S.C. 154(b) by 468 days.

(21) Appl. No.: 13/202,612

(22) PCT Filed: Feb. 25, 2010
(Under 37 CFR 1.47)

(86) PCT No.: PCT/US2010/025292
§ 371 (c)(1),
(2), (4) Date: Apr. 16, 2012

(87) PCT Pub. No.: WO2010/099247
PCT Pub. Date: Sep. 2, 2010

(65) Prior Publication Data
US 2012/0283840 A1    Nov. 8, 2012

Related U.S. Application Data

(60) Provisional application No. 61/155,060, filed on Feb. 24, 2009.

(51) Int. Cl.
A61F 2/32    (2006.01)
A61F 2/30    (2006.01)
A61B 17/86   (2006.01)
A61F 2/34    (2006.01)
A61B 17/02   (2006.01)
A61B 17/04   (2006.01)
A61F 2/46    (2006.01)
A61B 17/17   (2006.01)
A61B 17/84   (2006.01)

(52) U.S. Cl.
CPC ......... *A61F 2/34* (2013.01); *A61F 2002/30131* (2013.01); *A61F 2002/30192* (2013.01); *A61B 17/86* (2013.01); *A61F 2220/0075* (2013.01);
(Continued)

(58) Field of Classification Search
CPC ............... A61F 2/30; A61F 2/32; A61F 2/34; A61F 2/30734; A61F 2/30739; A61F 2002/34
USPC ........... 623/14.12, 22.14, 22.21–22.42, 22.11
See application file for complete search history.

(56) References Cited

U.S. PATENT DOCUMENTS 2,691,979 A    10/1954   Watson
3,740,769 A *  6/1973   Haboush .................... 623/22.36
(Continued)

FOREIGN PATENT DOCUMENTS

AU    2006334522    7/2007
AU    2008260279    12/2008
(Continued)

OTHER PUBLICATIONS

International Preliminary Report on Patentability dated Mar. 7, 2013 in Application No. PCT/US2011/049129.
(Continued)

*Primary Examiner* — Alvin Stewart
(74) *Attorney, Agent, or Firm* — Krieg DeVault LLP

(57) ABSTRACT

A partial rim implant for an acetabulum in a pelvic bone comprises a ridge, a bearing surface, and a fixation surface. The ridge is oriented to replace a labrum. The bearing surface is configured to align with the articulating surface of the acetabulum. The bearing surface extends from the ridge toward the apex of the acetabulum. The fixation surface is configured to fix the implant to a prepared bone surface of the pelvic bone.

33 Claims, 21 Drawing Sheets

(52) U.S. Cl.
CPC . *A61F 2230/0041* (2013.01); *A61F 2002/3487* (2013.01); *A61F 2002/30736* (2013.01); *A61F 2002/30578* (2013.01); *A61F 2002/3085* (2013.01); *A61B 2017/0275* (2013.01); *A61F 2250/0018* (2013.01); *A61F 2002/30576* (2013.01); *A61F 2002/30461* (2013.01); *A61B 17/0469* (2013.01); *A61F 2002/4658* (2013.01); *A61F 2/30728* (2013.01); *A61F 2002/3432* (2013.01); *A61B 17/1746* (2013.01); *A61F 2230/0013* (2013.01); *A61B 17/842* (2013.01); *A61F 2/4657* (2013.01); *A61F 2002/30014* (2013.01); *A61F 2002/30731* (2013.01)
USPC .................................................... 623/22.32

(56) References Cited

U.S. PATENT DOCUMENTS

| | | | | |
|---|---|---|---|---|
| 4,502,161 | A * | 3/1985 | Wall | 623/14.12 |
| 4,851,006 | A | 7/1989 | Tuke | |
| 4,919,667 | A * | 4/1990 | Richmond | 623/14.12 |
| 4,919,672 | A | 4/1990 | Millar et al. | |
| 4,955,919 | A | 9/1990 | Pappas et al. | |
| 4,959,072 | A * | 9/1990 | Morscher et al. | 623/22.33 |
| 5,047,062 | A | 9/1991 | Pappas et al. | |
| 5,067,964 | A * | 11/1991 | Richmond et al. | 623/14.12 |
| 5,127,920 | A * | 7/1992 | MacArthur | 623/22.11 |
| 5,133,764 | A * | 7/1992 | Pappas et al. | 623/23.14 |
| 5,176,711 | A * | 1/1993 | Grimes | 623/22.22 |
| 5,197,989 | A * | 3/1993 | Hinckfuss et al. | 623/22.42 |
| 5,376,122 | A * | 12/1994 | Pappas et al. | 623/22.28 |
| 5,376,125 | A | 12/1994 | Winkler et al. | |
| 5,609,646 | A * | 3/1997 | Field et al. | 623/22.32 |
| 5,735,900 | A * | 4/1998 | Barrett et al. | 128/898 |
| 5,766,262 | A * | 6/1998 | Mikhail | 623/23.25 |
| 5,871,548 | A * | 2/1999 | Sanders et al. | 623/22.36 |
| 5,879,404 | A | 3/1999 | Bateman et al. | |
| 5,880,976 | A | 3/1999 | DiGioia, III et al. | |
| 5,913,899 | A * | 6/1999 | Barrett et al. | 623/23.41 |
| 5,995,738 | A * | 11/1999 | DiGioia et al. | 703/11 |
| 6,002,859 | A | 12/1999 | DiGioia, III et al. | |
| 6,004,353 | A * | 12/1999 | Masini | 623/22.21 |
| 6,056,777 | A * | 5/2000 | McDowell | 623/18.11 |
| 6,120,546 | A * | 9/2000 | Dye et al. | 623/22.34 |
| 6,136,034 | A | 10/2000 | Townley | |
| 6,162,257 | A * | 12/2000 | Gustilo et al. | 623/22.32 |
| 6,171,340 | B1 * | 1/2001 | McDowell | 623/18.11 |
| 6,200,350 | B1 | 3/2001 | Masini | |
| 6,205,411 | B1 | 3/2001 | DiGioia, III et al. | |
| 6,299,647 | B1 | 10/2001 | Townley | |
| 6,306,173 | B1 * | 10/2001 | Masini | 623/22.32 |
| 6,383,224 | B1 * | 5/2002 | Gie et al. | 623/22.39 |
| 6,383,225 | B2 | 5/2002 | Masini | |
| 6,416,553 | B1 * | 7/2002 | White et al. | 623/22.38 |
| 6,475,243 | B1 * | 11/2002 | Sheldon et al. | 623/22.28 |
| 6,695,883 | B2 | 2/2004 | Crofford | |
| 6,758,864 | B2 * | 7/2004 | Storer et al. | 623/22.38 |
| 6,783,553 | B2 | 8/2004 | Grimes | |
| 6,908,486 | B2 * | 6/2005 | Lewallen | 623/22.21 |
| 6,923,833 | B2 | 8/2005 | Wasielewski | |
| 7,022,142 | B2 * | 4/2006 | Johnson | 623/22.24 |
| 7,060,102 | B2 | 6/2006 | Thompson et al. | |
| 7,074,241 | B2 | 7/2006 | McKinnon | |
| 7,104,995 | B2 | 9/2006 | Crofford | |
| 7,115,145 | B2 | 10/2006 | Richards | |
| 7,169,186 | B2 | 1/2007 | Harris et al. | |
| 7,291,176 | B2 | 11/2007 | Serra et al. | |
| 7,476,254 | B2 * | 1/2009 | White et al. | 623/22.32 |
| 7,611,541 | B2 | 11/2009 | Thompson et al. | |
| 7,615,083 | B2 * | 11/2009 | Wasielewski | 623/22.15 |
| 7,682,398 | B2 | 3/2010 | Croxton et al. | |
| 7,695,474 | B2 | 4/2010 | Crofford | |
| 7,708,783 | B2 | 5/2010 | Richards | |
| 7,722,678 | B2 * | 5/2010 | Brown et al. | 623/32 |
| 7,758,643 | B2 * | 7/2010 | Stone et al. | 623/14.12 |
| 7,819,918 | B2 * | 10/2010 | Malaviya et al. | 623/14.12 |
| 8,021,432 | B2 | 9/2011 | Meridew et al. | 623/22.32 |
| 8,048,166 | B2 * | 11/2011 | Brown et al. | 623/22.21 |
| 8,118,868 | B2 * | 2/2012 | May et al. | 623/13.14 |
| 8,292,967 | B2 * | 10/2012 | Brown et al. | 623/23.19 |
| 8,403,985 | B2 * | 3/2013 | Hodorek | 623/14.12 |
| 2001/0001121 | A1 | 5/2001 | Lombardo et al. | |
| 2002/0128653 | A1 | 9/2002 | Haidukewych | |
| 2002/0128720 | A1 | 9/2002 | Masini | |
| 2003/0187513 | A1 | 10/2003 | Durniak | |
| 2003/0212458 | A1 * | 11/2003 | Harris et al. | 623/22.17 |
| 2003/0212459 | A1 * | 11/2003 | Gibbs | 623/22.32 |
| 2004/0059416 | A1 * | 3/2004 | Murray et al. | 623/13.15 |
| 2004/0083004 | A1 * | 4/2004 | Wasielewski | 623/22.24 |
| 2004/0133979 | A1 | 7/2004 | Newkirk et al. | |
| 2004/0138757 | A1 | 7/2004 | Nadzadi et al. | |
| 2004/0153062 | A1 | 8/2004 | McGinley et al. | |
| 2004/0162621 | A1 | 8/2004 | Crofford | |
| 2004/0236341 | A1 | 11/2004 | Petersen | |
| 2005/0010232 | A1 | 1/2005 | Crofford | |
| 2005/0049714 | A1 | 3/2005 | Crofford | |
| 2005/0182493 | A1 * | 8/2005 | Bertram, III | 623/22.38 |
| 2005/0182496 | A1 | 8/2005 | Hunter et al. | |
| 2005/0203384 | A1 | 9/2005 | Sati et al. | |
| 2005/0245934 | A1 | 11/2005 | Tuke et al. | |
| 2006/0149389 | A1 * | 7/2006 | Romagnoli | 623/23.12 |
| 2006/0161167 | A1 | 7/2006 | Myers et al. | |
| 2006/0241780 | A1 | 10/2006 | McKinnon | |
| 2006/0264731 | A1 | 11/2006 | Murphy | |
| 2006/0293682 | A1 | 12/2006 | Justin et al. | |
| 2007/0032878 | A1 | 2/2007 | Bader et al. | |
| 2007/0083214 | A1 | 4/2007 | Duncan et al. | |
| 2007/0129809 | A1 * | 6/2007 | Meridew et al. | 623/22.32 |
| 2007/0135927 | A1 | 6/2007 | Harris et al. | |
| 2007/0161935 | A1 | 7/2007 | Torrie et al. | |
| 2007/0198022 | A1 | 8/2007 | Lang et al. | |
| 2007/0225818 | A1 | 9/2007 | Reubelt et al. | |
| 2007/0227024 | A1 * | 10/2007 | Beaule | 33/512 |
| 2007/0249967 | A1 | 10/2007 | Buly et al. | |
| 2007/0260256 | A1 | 11/2007 | Beaule | |
| 2007/0265635 | A1 | 11/2007 | Torrie et al. | |
| 2007/0299452 | A1 | 12/2007 | Curry | |
| 2008/0195221 | A1 | 8/2008 | Howald et al. | |
| 2008/0208200 | A1 | 8/2008 | Crofford | |
| 2008/0225818 | A1 | 9/2008 | Niu et al. | |
| 2008/0234685 | A1 | 9/2008 | Gjerde | |
| 2008/0243127 | A1 * | 10/2008 | Lang et al. | 606/87 |
| 2008/0281328 | A1 | 11/2008 | Lang et al. | |
| 2008/0281329 | A1 | 11/2008 | Fitz et al. | |
| 2008/0281426 | A1 | 11/2008 | Fitz et al. | |
| 2009/0069845 | A1 | 3/2009 | Frushell et al. | |
| 2009/0099570 | A1 | 4/2009 | Paradis et al. | |
| 2009/0112214 | A1 | 4/2009 | Philippon et al. | |
| 2009/0125108 | A1 * | 5/2009 | Linares | 623/14.12 |
| 2009/0131956 | A1 | 5/2009 | Dewey et al. | |
| 2009/0149965 | A1 | 6/2009 | Quaid | |
| 2009/0182340 | A1 | 7/2009 | Nikolchev et al. | |
| 2009/0192620 | A1 | 7/2009 | Ebbitt | |
| 2009/0198274 | A1 | 8/2009 | Frushell et al. | |
| 2009/0216113 | A1 | 8/2009 | Meier et al. | |
| 2009/0289806 | A1 | 11/2009 | Thornberry | |
| 2009/0306586 | A1 | 12/2009 | Ross et al. | |
| 2009/0316967 | A1 | 12/2009 | Dardenne et al. | |
| 2009/0319051 | A9 * | 12/2009 | Nycz et al. | 623/23.57 |
| 2010/0016892 | A1 | 1/2010 | Kaiser et al. | |
| 2010/0086186 | A1 | 4/2010 | Zug et al. | |
| 2010/0114101 | A1 | 5/2010 | Crofford | |
| 2010/0152859 | A1 | 6/2010 | Thompson et al. | |
| 2011/0190887 | A1 * | 8/2011 | Shapiro | 623/14.12 |
| 2011/0238180 | A1 * | 9/2011 | Fritz et al. | 623/14.12 |
| 2011/0288643 | A1 * | 11/2011 | Linder-Ganz et al. | 623/14.12 |
| 2012/0053590 | A1 * | 3/2012 | Allen et al. | 606/87 |
| 2012/0109331 | A1 * | 5/2012 | Meridew et al. | 623/22.21 |
| 2012/0232656 | A1 * | 9/2012 | Gedet et al. | 623/14.12 |
| 2012/0232657 | A1 * | 9/2012 | Myung et al. | 623/14.12 |
| 2012/0283840 | A1 * | 11/2012 | Frederick et al. | 623/22.32 |
| 2013/0006276 | A1 * | 1/2013 | Lantz et al. | 606/144 |
| 2013/0035766 | A1 * | 2/2013 | Meridew | 623/22.21 |
| 2013/0211536 | A1 * | 8/2013 | Metzger et al. | 623/23.5 |

(56) References Cited

U.S. PATENT DOCUMENTS

| | | | |
|---|---|---|---|
| 2013/0218283 A1* | 8/2013 | Samuelson et al. | 623/20.29 |
| 2013/0226311 A1* | 8/2013 | Bonutti | 623/23.58 |
| 2013/0245780 A1* | 9/2013 | Meridew et al. | 623/22.21 |

FOREIGN PATENT DOCUMENTS

| | | |
|---|---|---|
| CH | 449174 | 12/1967 |
| EP | 0289192 | 11/1988 |
| EP | 0803234 | 10/1997 |
| EP | 1195149 | 4/2002 |
| EP | 1437987 | 7/2004 |
| EP | 1472997 | 11/2004 |
| EP | 1472998 | 11/2004 |
| EP | 1263350 | 1/2005 |
| EP | 1493406 | 1/2005 |
| EP | 1506749 | 2/2005 |
| EP | 1520559 | 4/2005 |
| EP | 1550024 | 7/2005 |
| EP | 1553898 | 7/2005 |
| EP | 1673043 | 6/2006 |
| EP | 1494625 | 8/2006 |
| EP | 1713420 | 10/2006 |
| EP | 1304980 | 5/2007 |
| EP | 1945146 | 7/2008 |
| EP | 1954235 | 8/2008 |
| EP | 1981409 | 10/2008 |
| EP | 1996123 | 12/2008 |
| EP | 1628590 | 4/2009 |
| EP | 2124764 | 12/2009 |
| EP | 2152219 | 2/2010 |
| EP | 1499268 | 4/2010 |
| EP | 2175419 | 4/2010 |
| EP | 2185108 | 5/2010 |
| GB | 2139098 | 11/1984 |
| JP | 2009525767 | 7/2009 |
| WO | WO88/07356 | 10/1988 |
| WO | WO01/67999 | 9/2001 |
| WO | WO02/09615 | 2/2002 |
| WO | WO02/09616 | 2/2002 |
| WO | WO03/034952 | 5/2003 |
| WO | WO03/086242 | 10/2003 |
| WO | WO03/086243 | 10/2003 |
| WO | WO03/094802 | 11/2003 |
| WO | WO04/001569 | 12/2003 |
| WO | WO2004/037129 | 5/2004 |
| WO | WO2005/000140 | 1/2005 |
| WO | WO2005/039453 | 5/2005 |
| WO | WO2005/072231 | 8/2005 |
| WO | WO2006/030392 | 3/2006 |
| WO | WO2007/021806 | 2/2007 |
| WO | WO2007/056678 | 5/2007 |
| WO | WO2007/080454 | 7/2007 |
| WO | WO2007/092841 | 8/2007 |
| WO | WO2007/109291 | 9/2007 |
| WO | WO2008/090468 | 7/2008 |
| WO | WO2008/112996 | 9/2008 |
| WO | WO2008/130656 | 10/2008 |
| WO | WO2008/150731 | 12/2008 |
| WO | WO2009/039513 | 3/2009 |
| WO | WO2009/046547 | 4/2009 |
| WO | WO2009/058830 | 5/2009 |
| WO | WO2009/076293 | 6/2009 |
| WO | WO2009/076297 | 6/2009 |
| WO | WO2009/108683 | 9/2009 |
| WO | WO2009/114829 | 9/2009 |
| WO | WO2010/033473 | 3/2010 |
| WO | WO2010/052500 | 5/2010 |
| WO | WO2010/065901 | 6/2010 |
| WO | WO2010/096124 | 8/2010 |
| WO | WO2010/099247 | 9/2010 |

OTHER PUBLICATIONS

International Search Report and Written Opinion dated Mar. 27, 2012 in Application No. PCT/US2011/049129.
International Search Report for PCT/US2009/056890, mailed Apr. 5, 2010.
International Preliminary Report on Patentability and Written Opinion for PCT/US2009/056890, mailed Mar. 22, 2011.
International Search Report and Written Opinion for PCT/US2010/025292, mailed Dec. 28, 2010.
International Preliminary Report on Patentability and Written Opinion for PCT/US2010/025292, mailed Aug. 30, 2011.
International Search Report for PCT/IB2006/004038, mailed Aug. 29, 2007.
Byrd, et al., "Arthroscopic Management of Femoracetabular Impingement," AAOS Instructure Course Lectures, vol. 58, 2009, pp. 231-239.
Leunig, et al., "Femoracetabular Impingement: Etiology and Surgical Concept," Operative Techniques in Orthopaedics, Jun. 5, 2005, pp. 247-255.
Leunig, et al. "Femoracetabular Impingement: Treatment of the Acetabular Side," AAOS Instructional Course Lectures, vol. 58, 2009, pp. 223-229.
Clohisy, et al., "Treatment of Anterior Femoroacetabular Impingement with Combined Hip Arthroscopy and Limited Anterior Decompression," The Iowa Orthopaedic Journal, vol. 25, undated, pp. 164-171.
European Office Action; European Patent Office; European Patent Application No. 10746801.9; Aug. 20, 2014; 8 pages.

* cited by examiner

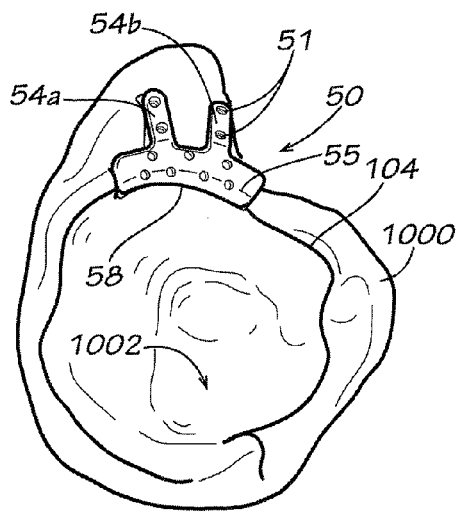
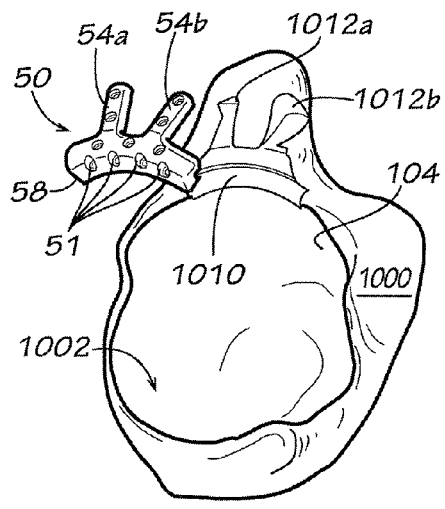
FIG. 9A  FIG. 9B
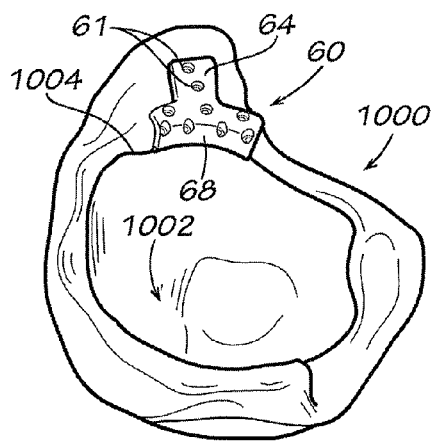
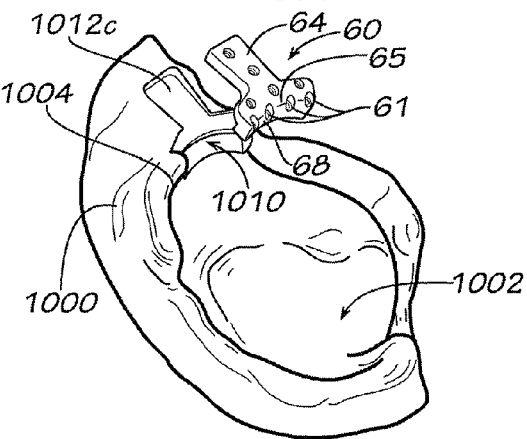
FIG. 10A  FIG. 10B
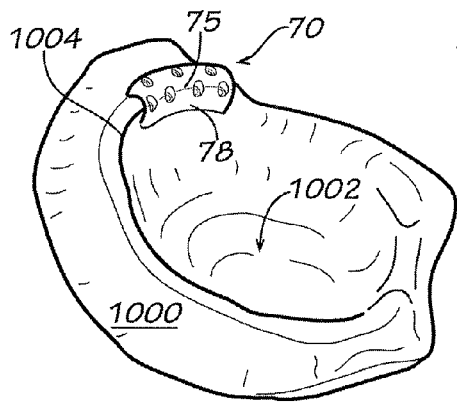
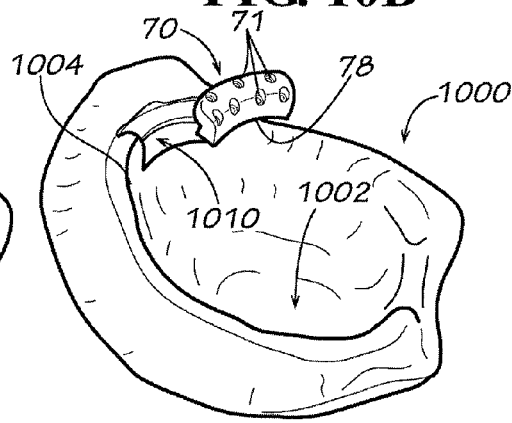
FIG. 11  FIG. 12

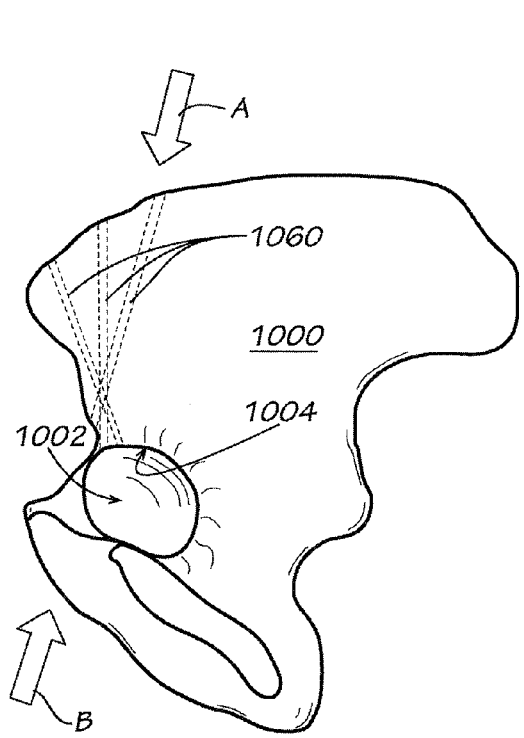
FIG. 41
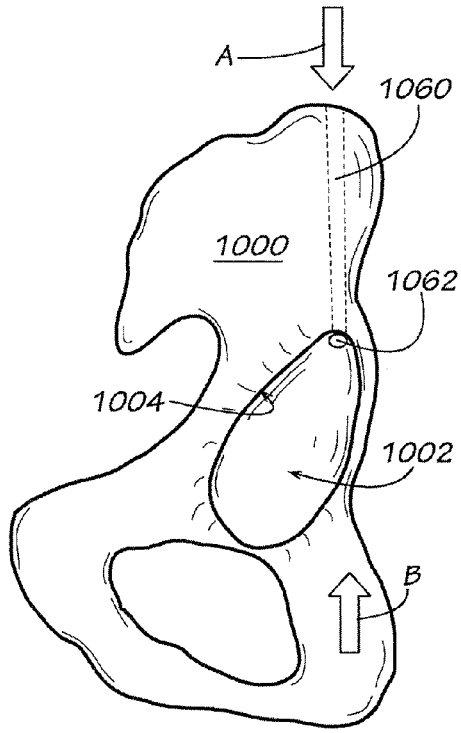
FIG. 42
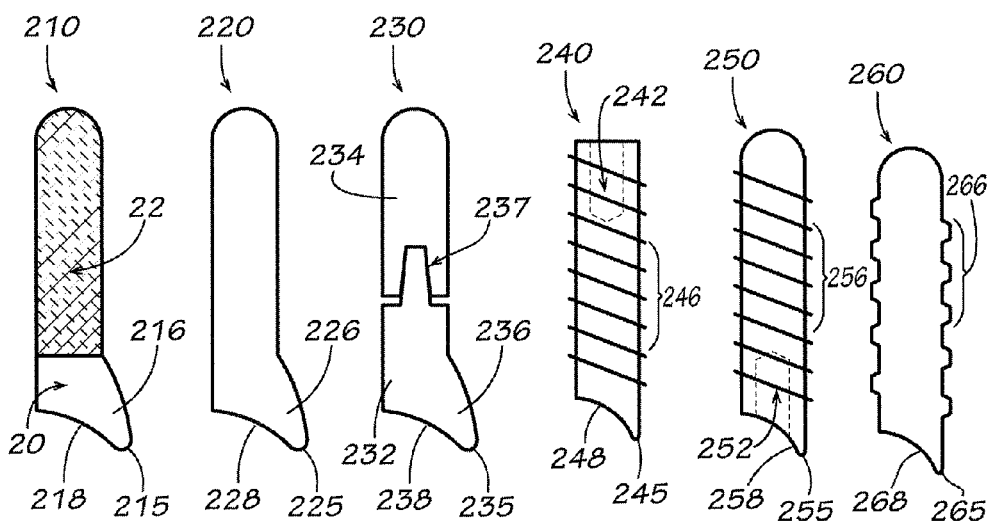
FIG. 43A FIG. 43B FIG. 43C FIG. 43D FIG. 43E FIG. 43F

METHODS AND APPARATUS FOR FAI SURGERIES

CROSS-REFERENCE TO RELATED APPLICATIONS

This application is the U.S. national phase of International Application No. PCT/US2010/025292, filed Feb. 25, 2010 and published in English on Sep. 2, 2010 as International Publication No. WO 2010/099247 A2, which application claims the benefit of U.S. Provisional Application No. 61/155,060, filed Feb. 24, 2009, the contents of both of which are incorporated herein by reference.

BACKGROUND

1. Field

This invention relates generally to hip surgeries and, more particularly, relates to surgical methods, tools and implants for treating femoral acetabular impingement.

2. Related Art

Femoroacetabular impingement or FAI is a condition of the hip joint where the femoral head and acetabulum rub abnormally creating damage to the hip joint. The damage can occur to the articular cartilage of the head or acetabulum or to the labral cartilage on and around the acetabular rim.

Specifically, FAI may take one of two forms: cam or pincer. The difference between the two forms is determined by the abnormality of the hip joint that is the cause of the damage. The cam form of FAI occurs when the femoral head and neck relationship is aspherical, or not perfectly round. This loss of roundness contributes to abnormal contact between the head and socket. The pincer form occurs when the the acetabulum has too much coverage of the femoral head. This over-coverage typically exists along the front-top rim of the acetabulum and results in the labral cartilage being "pinched" between the rim of the socket and the anterior femoral head-neck junction. In most cases, the cam and pincer forms exist together (thus creating a compound form of FAI).

Treatment of FAI may be accomplished by surgical intervention. Arthroscopically, the hip may be scoped to assess the hip joint and treat damage that is found through two to four 1 cm incisions. Often, all of the components of FAI such as the labral tear, damaged cartilage, and friction between the ball and socket can be treated through the arthroscope. Repair may include debridement, microfracture techniques, labral repair, and bony decompression. Care must be taken to avoid damage to the hip's blood supply during the osteoplasty procedure.

An open surgical technique requires hip dislocation through an incision (approximately 6 to 10 inches). An upper thigh bone osteotomy allows for dislocation of the femoral head from the socket exposing all parts of the joint. This exposure allows treatment of labral tears and abnormal contact between the ball and socket while protecting the blood supply to the hip. In both of these types of treatment, bone removal and repair are employed to address FAI.

SUMMARY OF THE INVENTION

It is in view of the above that the present invention was developed. In one embodiment of the invention, a partial rim implant for an acetabulum in a pelvic bone comprises a ridge, a bearing surface, and a fixation surface. The ridge is oriented to replace a labrum. The bearing surface is configured to align with the articulating surface of the acetabulum. The bearing surface extends from the ridge toward the apex of the acetabulum. The fixation surface is configured to fix the implant to a prepared bone surface of the pelvic bone.

In another aspect of the invention, the fixation surface is generally perpendicular to the articulating surface of the acetabulum.

In yet another aspect of the invention, the apex of the acetabulum has a central axis extending toward a plane defined by the rim of the acetabulum, further comprising a rim portion extending from the fixation portion to the ridge, the rim portion orienting the ridge.

Another embodiment provides an implant made of a first compliant material and a second stiffer material.

In another embodiment, the ridge of the implant is made of the first compliant material.

In yet another embodiment, the fixation surface is made of the first compliant material.

Another embodiment comprises an insertion portion extending generally perpendicularly from the bearing surface and a fixation flange extending from a rim portion of the implant. The insertion portion and the flange portion converge toward one another as the flange and insertion portion extend away from the acetabulum.

In another embodiment, the apex of the acetabulum has a central axis extending toward a plane defined by the rim of the acetabulum, the implant further comprising a transition portion located between the bearing portion and the rim portion, the transition portion extends the rim portion toward the central axis of the acetabulum.

In yet another embodiment, the implant is rolled onto the rim of the acetabulum.

Another embodiment provides a fixation surface which is a post extending into the pelvic bone.

In another embodiment, the implant is fixed to the bone with sutures.

Another aspect of the invention provides a spacer for spacing a femur from an acetabulum. The spacer comprises a spoon and a plenum. The spoon portion is configured to wrap around the head of the femur. The plenum is attached to the spoon and configured to inflate the spoon. The spoon, when inflated, separates the acetabulum from the femur.

In another embodiment, the spoon further comprises a cutout portion configured to extend around the ligamentum teres.

In yet another embodiment, the spacer further comprises a stiff portion extending through the spoon, such that the spoon may be pushed into the hip joint.

Another embodiment provides for the stiff portion to extend around the periphery of the spoon.

Another aspect of the invention provides a cutting guide for cutting a portion of a rim of an acetabulum. The guide comprises a generally planar rectangular member and an axis. The generally rectangular planar member has an opening in the central portion. Edges of the opening form a cutting surface. The opening has a width and a height. The axis extends across the planar member. The axis forms a fold line upon which the planar member may be folded such that when the planar member is folded over an acetabular rim, the edges of the opening extend over the rim and are configured to direct a cutting member to remove bone to a depth defined by the height of the opening.

In another embodiment, the width of the opening is set to the width of the implant.

In yet another embodiment, the fold line is curved.

Another embodiment provides the curved fold line is curved relative to the radius of the acetabulum.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings:

FIG. 9A is a view of another embodiment of an acetabular implant for treating FAI implanted on an acetabulum;

FIG. 9B is an exploded view of the acetabulum and implant of FIG. 9A;

FIG. 10A is a view of another embodiment of an acetabular implant for treating FAI implanted on an acetabulum;

FIG. 10B is an exploded view of the acetabulum and implant of FIG. 10A;

FIG. 11 is a view of another embodiment of an acetabular implant for treating FAI implanted on an acetabulum;

FIG. 12 is an exploded view of the acetabulum and implant of FIG. 11;

FIG. 41 is a view of an acetabulum showing pathways from the iliac crest to labral or acetabular defects;

FIG. 42 is another view of the acetabulum of FIG. 41 showing pathways from the iliac crest to labral or acetabular defects;

FIGS. 43A to 43F are views of different embodiments of acetabular implants to insert into the pathways shown in FIG. 41 and FIG. 42.

DETAILED DESCRIPTION OF THE EMBODIMENTS

Figure 1:
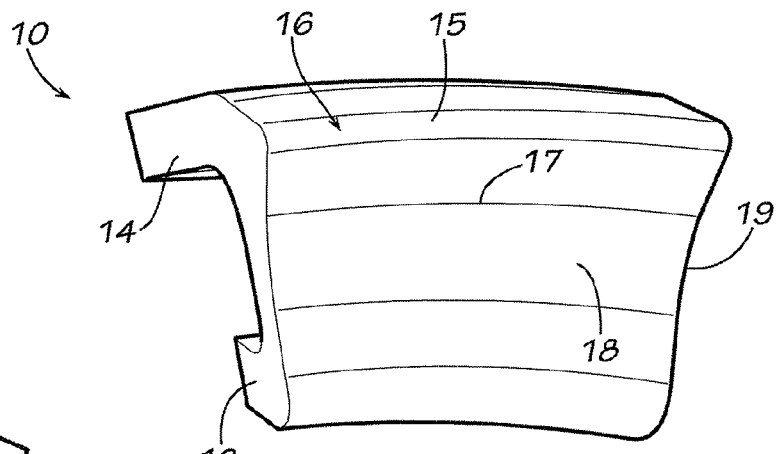
FIG. 1 is a view of an embodiment of an acetabular implant for treating FAI.
Figure 2:
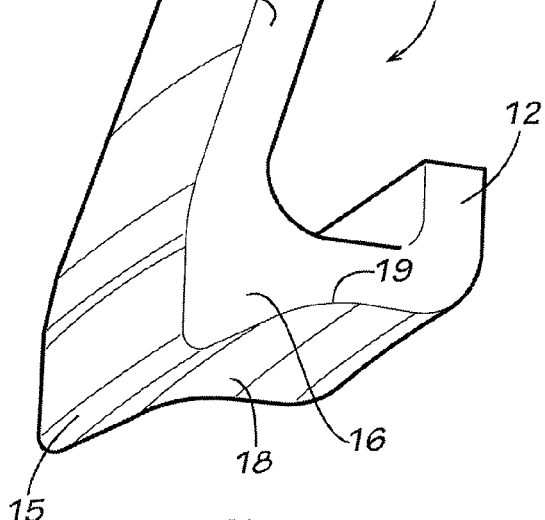
FIG. 2 is another view of the embodiment of FIG. 1.
Figure 3:
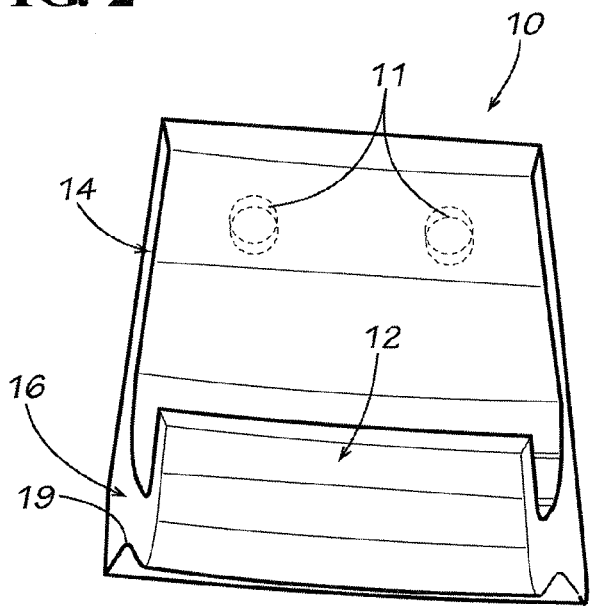
FIG. 3 is another view of the embodiment of FIG. 1.

Referring to the accompanying drawings in which like reference numbers indicate like elements, FIG. 1 is a view of an embodiment of an acetabular implant 10 for treating FAI. The implant 10 has an insertion portion 12, a flange portion 14, a ridge 15, a rim portion 16, a rim curvature 17, a bearing surface 18 and a rim-bearing transition 19. For additional views of this embodiment, FIG. 2 is another view of the embodiment of FIG. 1 and FIG. 3 is yet another view of the embodiment of FIG. 1. In FIG. 3, mounting holes 11 are positioned on the flange portion 14. The insertion portion 12 may be configured to insert into the acetabulum generally perpendicular to the bearing surface of the acetabulum. The bearing surface 19, then, would lie generally flush with the bearing surface of the acetabulum. The rim-bearing transition 19 may generally be a curved portion of the bearing surface 19 that transitions the bearing surface 19 into the rim portion 16. The rim portion 16 extends inward toward a central axis of the acetabulum from the bearing surface 19. This rim portion 16 may then be used to help capture the head of the femur (which was the function of the surface that was removed, albeit the removed surface was damaged necessitating its removal. Thus, the implant may restore the function of the damaged surfaces that were removed without causing the negative pathological response that was generated from the damaged tissue, bone or cartilage.

The rim portion 16 has a ridge that transitions the rim portion 16 from the bearing surface side of the implant 10 to a fixation side (through the flange portion 14). The flange portion 14 may be fixed to the acetabulum by screws or pins through screw holes 11 (as shown in this embodiment) or by other means as discussed with respect to other embodiments. The rim curvature 17 of the implant 10 is sized to fit the acetabulum. Thus, varying diameters of different acetabulums may require various rim curvatures 17 of the implant. Additionally, depending on the size of the damaged region, the thickness of the implant 10, the width of the implant 10 and the depth of the rim portion 16 may be changed to fit the specific anatomy of the patient.

The embodiments generally share some common features, namely, a bearing portion, a rim portion for replacing the labrum, and a fixation portion. It is contemplated within the scope of this disclosure that different variations as described herein may achieve a desired implant embodiment by providing these features as described and then combined.

Figure 4A:
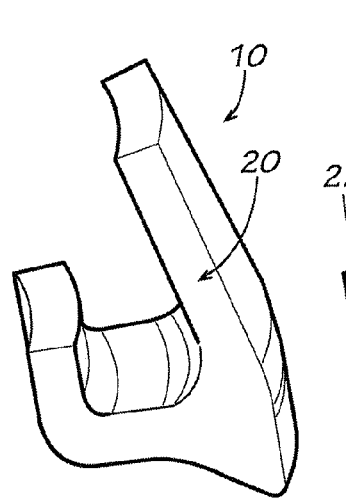
FIGS. 4A through 4F are views of embodiments of an acetabular implant similar to the embodiment of FIG. 1.
Figure 4B:
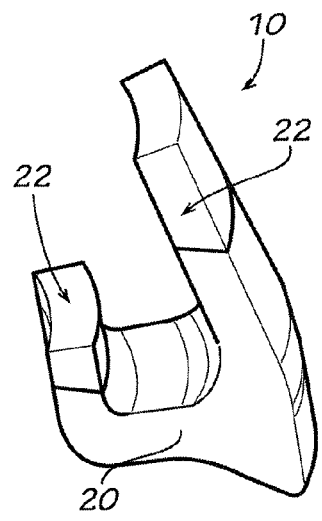
Figure 4C:
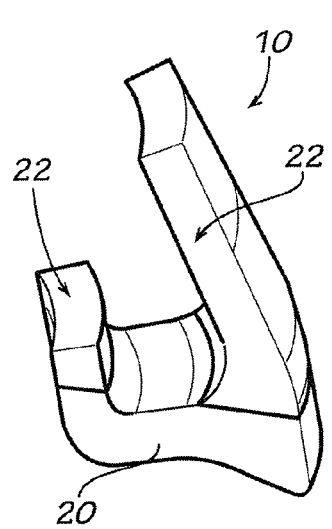
Figure 4D:
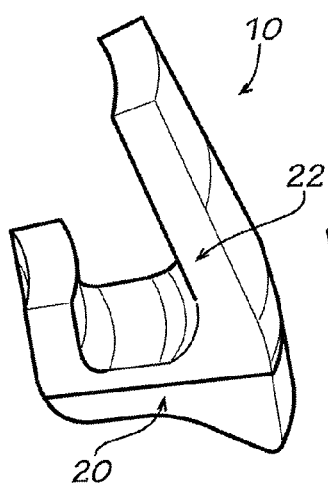
Figure 4E:
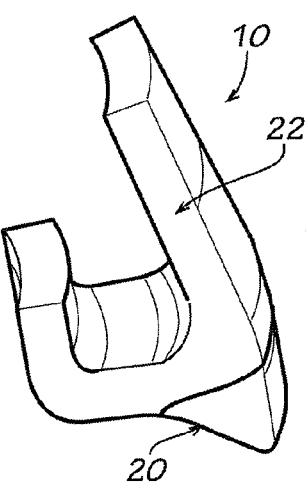
Figure 4F:
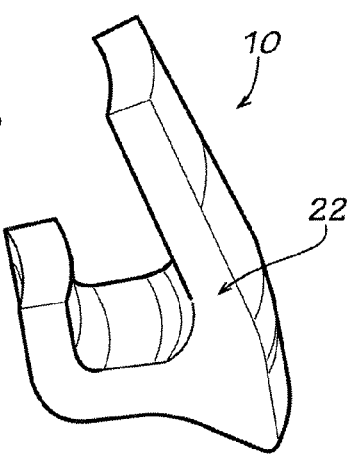

FIGS. 4A through 4F are views of embodiments of acetabular implant 10 similar to the embodiment of FIG. 1. These embodiments allow for different materials to be used for different regions of the implant 10. A first stiffer material portion 20 (e.g. metal, porous material, or PEEK) may be used for portions of the bearing surface while a more flexible, compliant material portion 22 (e.g., polyurethane) may be used for the flanges and bone interfacing surfaces. Such embodiments may give the structure necessary to perform the functions of the implant 10 while allowing for a more conforming contact surface between the implant and the acetabulum. The amount of one type of material vrealtive to the other may be determined by the dynamics of the particular joint. For example, in FIG. 4B, the majority of the implant is made from the stiffer material 20. In such an embodiment, the dynamics may produce larger loads across the implant than an implant such as the one shown in FIG. 4E, where only the rim portion is made of the stiffer material 20. A continuum between exerted loads, implant stiffness, and conformity may all contribute to the material composition of the implant 10 such that an implant may be made from a stiffer material 20 (shown in FIG. 4A) or entirely from the more compliant material (as shown in FIG. 4F).

Figure 5B:
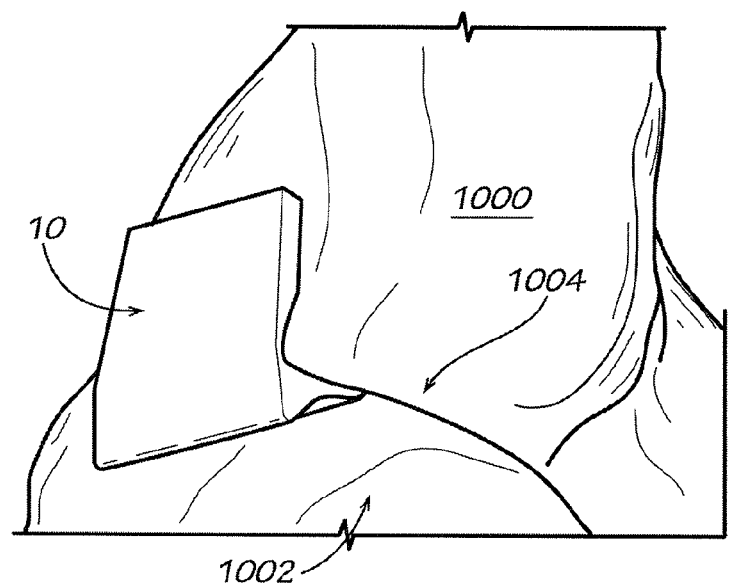
FIGS. 5A and 5B are views of the implant of FIG. 1 on an acetabulum.
Figure 5A:
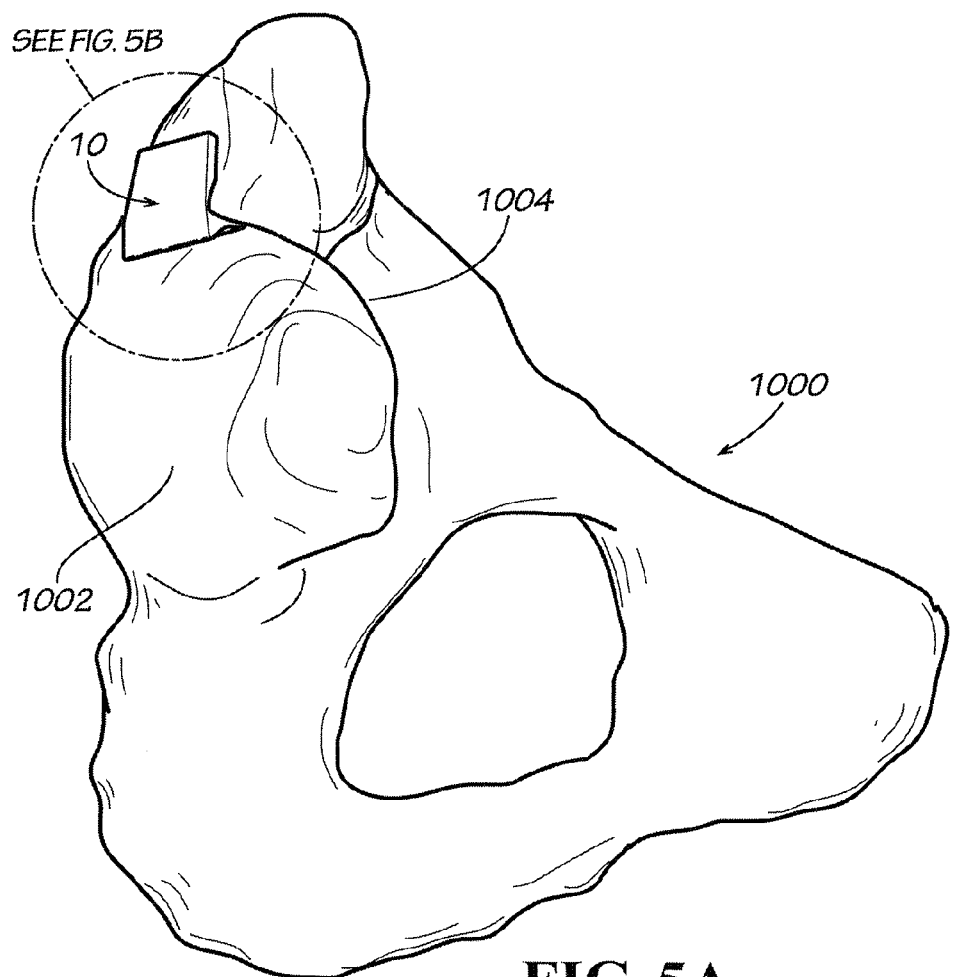

FIGS. 5A and 5B are views of the implant 10 of FIG. 1 on an acetabular rim 1004 in the acetabulum 1002 of a pelvic bone 1000. As previously described, the implant 10 extends over the rim of the acetabulum 1004. The rim portion 16 of the implant 10 is positioned to generally extend toward a central axis of the acetabulum (or at least to not continue to extend the spherical features of the acetabulum more.) As shown in this embodiment, there are no screw holes extending through the flange portion of the implant 10. Fixation means, if necessary, may be accomplished through a bone ingrowth surface on the implant 10, or by other mechanical means.

Figure 6:
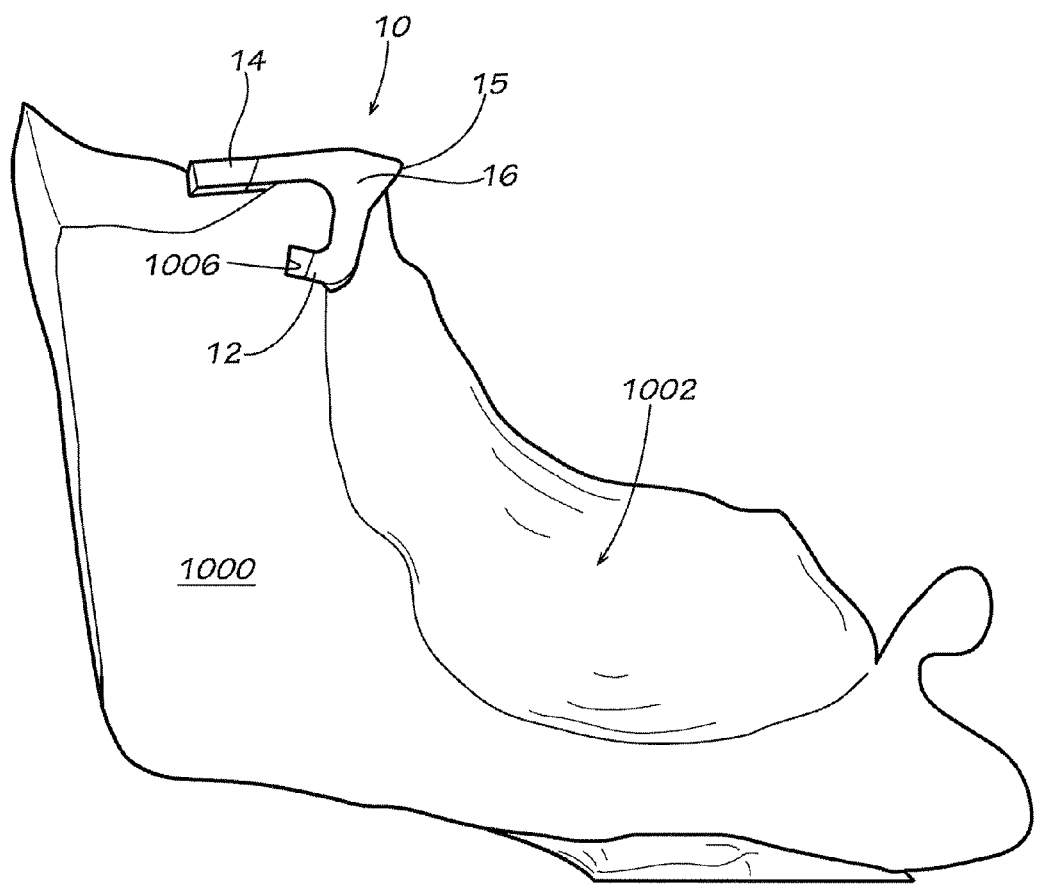
FIG. 6 is a cut away view of the implant and acetabulum of FIG. 5.

FIG. 6 is a cut away view of the implant and acetabulum of FIG. 5. The implant 10 is fixed to the acetabulum by a mechanical interference fit. The portions 12 and 14 converge toward one another in the pelvic bone. Thus, once the implant is put on the bone, the implant will not dislodge as the converging surfaces grip the bone in between the insertion portion 12 and the flange 14. Such an interference fit may be achieved by rolling the implant 10 from inside the acetabulum 1002 over the rim. Such a method requires the insertion portion 12 to first engage the bone, then rolling the flange 14 over the top of the bone.

Figure 7A:
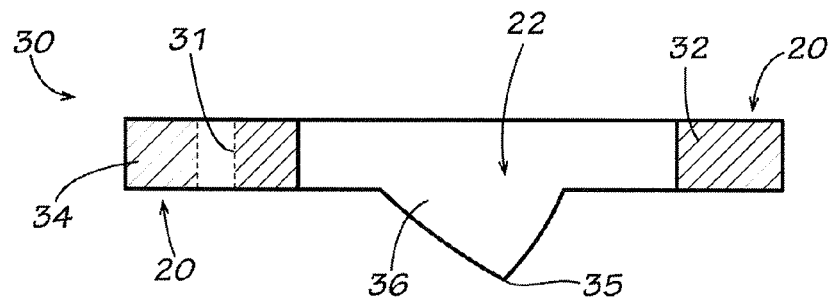
FIG. 7A is a view of another embodiment of an acetabular implant for treating FAI.
Figure 7B:
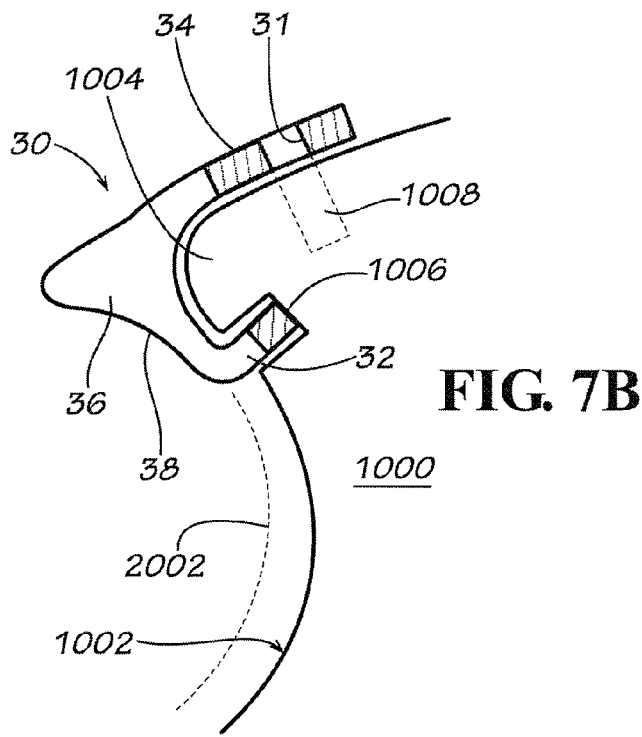
FIGS. 7B and 7C are views of the embodiment of FIG. 7A attached to an acetabulum.
Figure 7C:
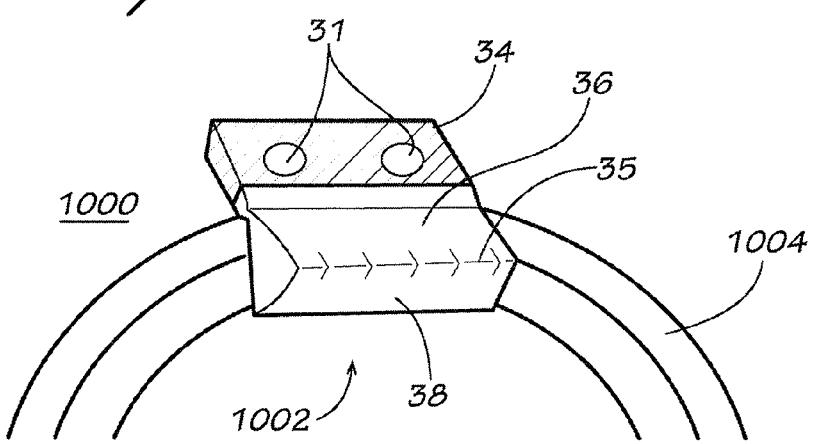

FIG. 7A is a view of another embodiment of an acetabular implant for treating FAI. This bi-material implant 30 also has stiffer portions 20 and more flexible portions 22. The more flexible portions, however, comprise the fixation portions of the implant 30, which in this example is the insertion portion 32 and the flange portion 34. The implant 30, then may be wrapped around the rim of the acetabulum. As shown in FIGS. 7A and 7B, FIGS. 7B and 7C are views of the embodiment of FIG. 7A attached to an acetabulum 1000. The insertion portion 32 may be put into a prepared recess portion 1006 of the acetabulum. The flexible portion 22 may then be wrapped around the rim and fixed to the acetabulum (for example through a mounting hole 31) to the acetabulum 1000. A more flexible bearing portion 38 and rim portion 36 may then be positioned to adjust to the proper depth to keep the bearing surface 38 of the implant 30 in line with the natural bearing surface of the acetabulum and may also position a ridge 35 of the rim portion 36 to be properly oriented to provide the capture features that are replaced with the implant 30.

Figure 8B:
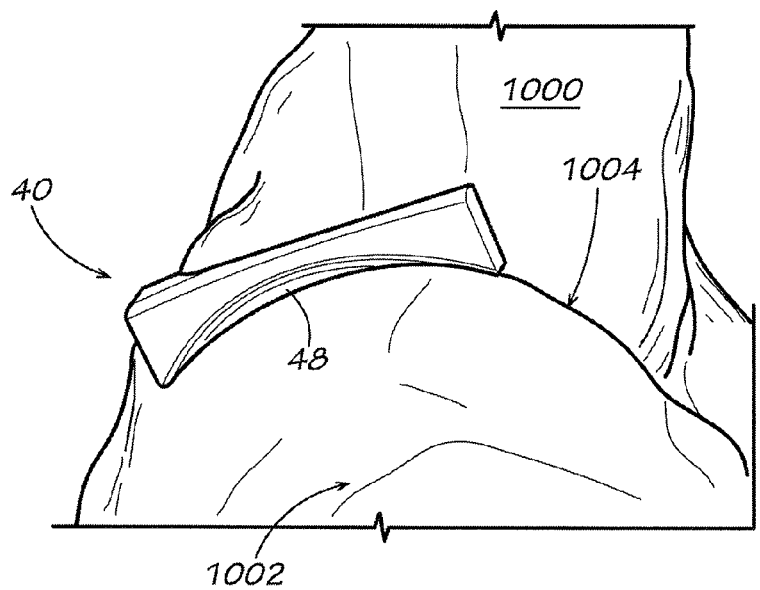
FIGS. 8A and 8B are views of another embodiment of an acetabular implant for treating FAI implanted on an acetabulum.
Figure 8A:
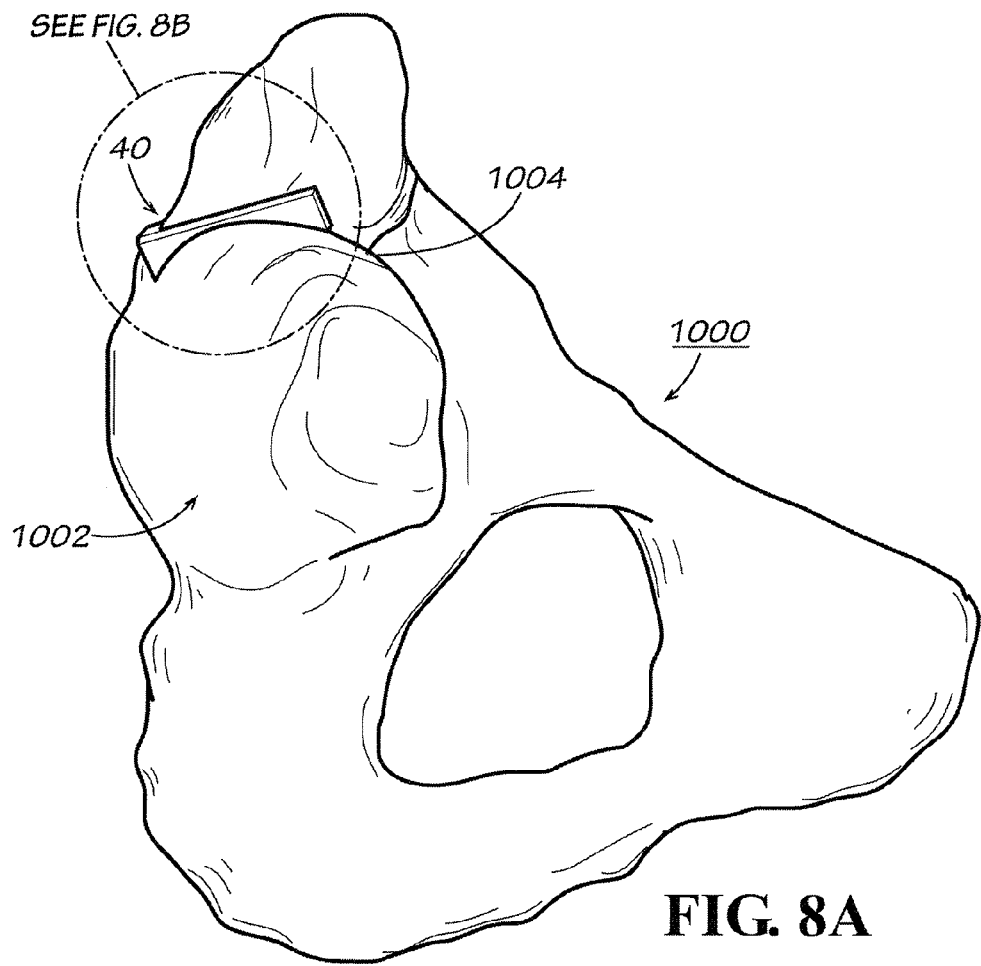

FIGS. 8A and 8B are views of another embodiment of an acetabular implant 40 for treating FAI implanted on an acetabulum 1002. This embodiment may be a hard bearing material (such as Oxinium) that may be press fit into the bone. Such an embodiment may require very precise bone preparation and a specifically sized match for the shape of the preparation accounting for the natural characteristics of the acetabulum 1002. The bearing surface 48 of the implant 40 may then be a hard bearing just as the whole implant 40 is a hard material. The bone for receiving such an implant may be prepared with an instrument having the shape desired for the bone contacting surface of the implant 40 so that the preparation may occur at one time, instead of a more fitted procedure where different portions of bone may be prepared based upon earlier preparation of other bone portions. The implant 40 may be under constant compressive load so that there is little risk of dislodging of the implant 40 from the acetabulum.

FIG. 9A is a view of another embodiment of an acetabular implant 50 for treating FAI implanted on an acetabulum. FIG. 9B is an exploded view of the acetabulum and implant 50 of FIG. 9A. Mounting holes 51 may be positioned on flanges 54a and 54b to mount the implant 50 to the bone. A ridge 55 on a rim portion of the implant 50 provides the constraining feature of the implant 50. A bearing surface 58 extends into the acetabulum to mate with the natural bearing surface of the acetabulum. In the cutaway view of FIG. 9B, bone preparation surfaces 1010, 1012a and 1012b are prepared to receive the implant 50.

FIG. 10A is a view of another embodiment of an acetabular implant 60 for treating FAI implanted on an acetabulum. FIG. 10B is an exploded view of the acetabulum and implant 60 of FIG. 10A. Mounting holes 61 may be positioned on flange 64 to mount the implant 60 to the bone. A ridge 65 on a rim portion of the implant 60 provides the constraining feature of the implant 60. A bearing surface 68 extends into the acetabulum to mate with the natural bearing surface of the acetabulum. In the cutaway view of FIG. 9B, bone preparation surfaces 1010, 1012c are prepared to receive the implant 60.

FIG. 11 is a view of another embodiment of an acetabular implant 70 for treating FAI implanted on an acetabulum. FIG. 12 is an exploded view of the acetabulum and implant 70 of FIG. 11. Mounting holes 71 may be positioned on the implant 70 to mount the implant 70 to the bone. A ridge 75 on a rim portion of the implant 70 provides the labrum replacement feature of the implant 70. A bearing surface 78 extends into the acetabulum to mate with the natural bearing surface of the acetabulum. In the cutaway view of FIG. 9B, bone preparation surfaces 1010 are prepared to receive the implant 70.

In the embodiments of FIG. 9A through FIG. 12, the bone preparation matches the implant surfaces without a compliant material in use. Thus the bone preparation would likely be from guided stamps or cutting surfaces, and not from free hand cutting using burrs or the like. As the prepared surfaces direct the position of the entire implant, the prepared surfaces must take into account not only the underlying bone but also the rim characteristics and bearing surface characteristics of the implant.

Figure 13:
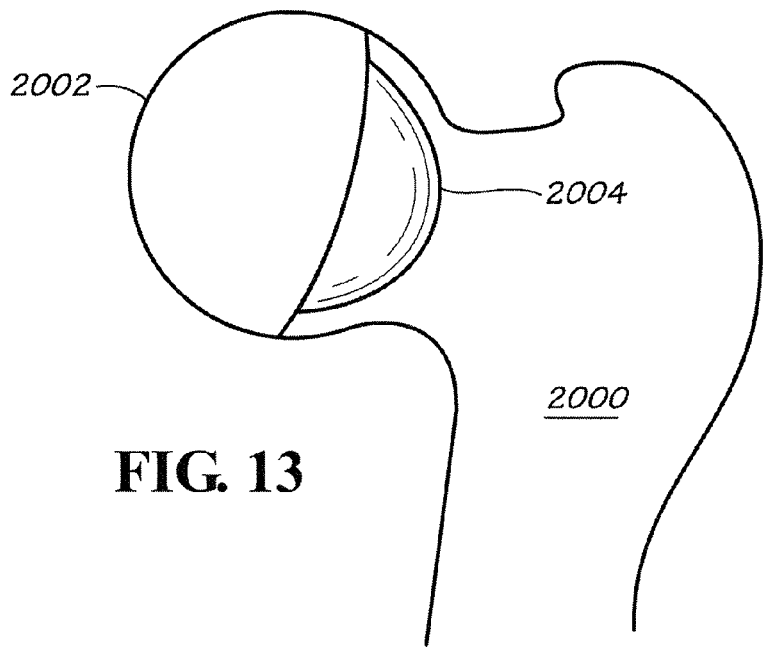
FIG. 13 is a view of a femur showing the affected area for cam type FAI.
Figure 14A:
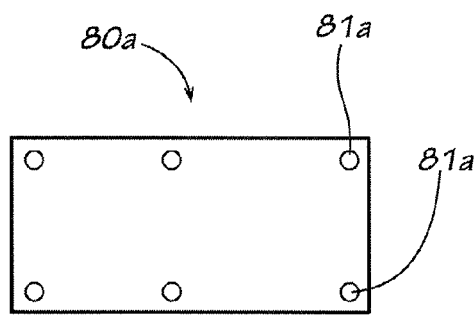
FIGS. 14A through 14D are views of embodiments of femoral implants for treating FAI on the femur.
Figure 14B:
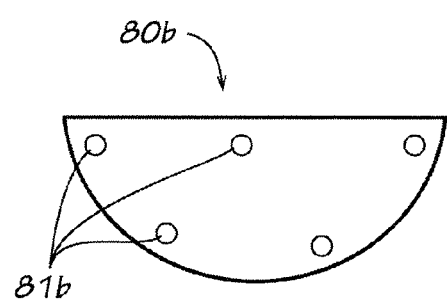
Figure 14C:
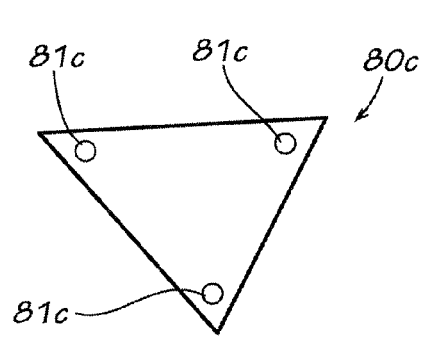
Figure 14D:
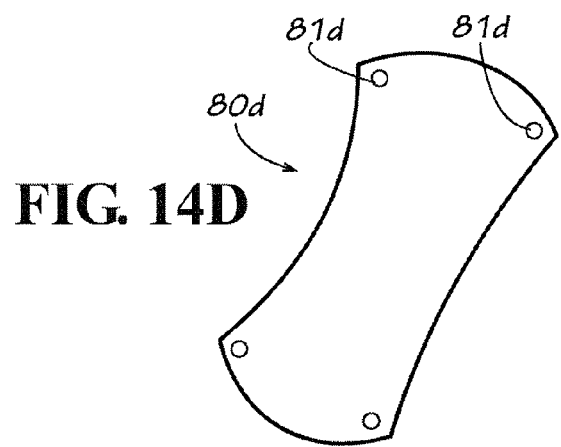

FIG. 13 is a view of a femur 2000 showing an affected area 2004 for cam type FAI. An aspherical femoral head 2002 may create the affected area 2004. It may be necessary to treat the affected area first with debridement and then with an implant designed to limit osseus overgrowth (as would occur from continued stress from contact with the acetabulum. FIGS. 14A through 14D are views of embodiments of femoral implants 80a, 80b, 80c, and 80d for treating FAI on the femur. Mounting holes 81a, 81b, 81c, and 81d may be used to mount the implant onto the femur. Alternatively, the implant shape may be molded intraoperatively or from radiographic scans of the femur prior to surgery. The implants may be made of a rigid or flexible material and mounted with any of the mounting means discussed herein.

Figure 15:
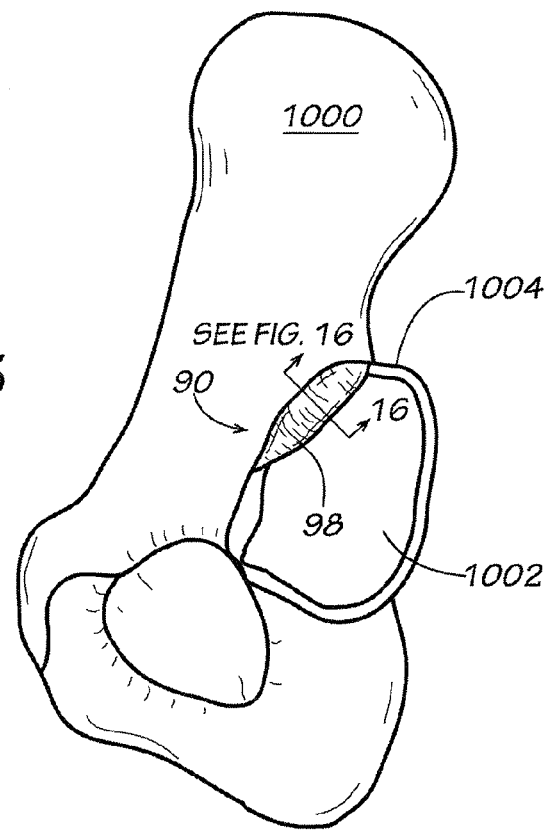
FIG. 15 is a view of another embodiment of an acetabular implant for treating FAI implanted on an acetabulum.
Figure 16:
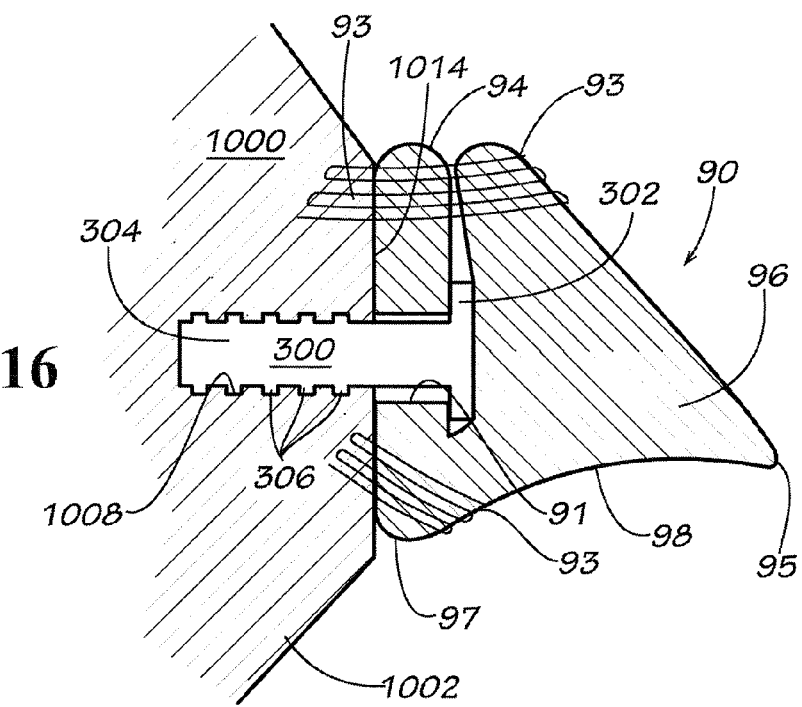
FIG. 16 is a cutaway view of the embodiment of FIG. 15.

FIG. 15 is a view of another embodiment of an acetabular implant 90 for treating FAI implanted on an acetabulum. FIG. 16 is a cutaway view of the embodiment of FIG. 15. The implant 90 is made from a flexible material that may bend at a transition 97 so that a screw 300 having a head 302 greater in diameter than a hole 91 through a flange portion 94 of the implant 90 may fix the implant to the bone. A ridge 95 of a rim portion 96 replaces the labrum. A bearing surface 98 contacts the femoral head. The transition 97 also transitions the bearing surface between the acetabulum 1002 and the bearing surface 98 of the implant 90.

The bone preparation may include a single planar surface cutting a portion of the rim of the acetabulum away. The screw 300, then, may compress the flange 94 against a bone surface 1014 to fix the implant 90 to the bone through fixation elements 306 on a shaft 304 of the screw 300. The rim portion 96 of the implant 90 may then be moved into position over the screw head 302. The rim portion 96 may also be fixed to the flange 94 with sutures or other fixation elements so that the rim portion 96 is stiffened relative to the flange 94.

Figure 17:
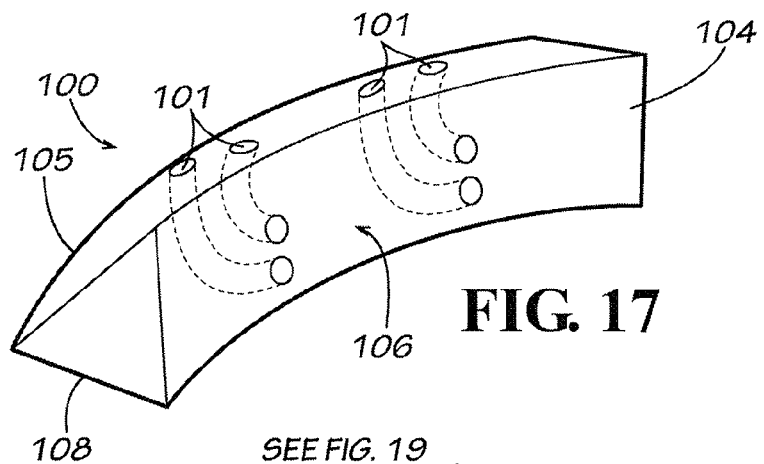
FIG. 17 is a view of another embodiment of an acetabular implant for treating FAI.
Figure 18:
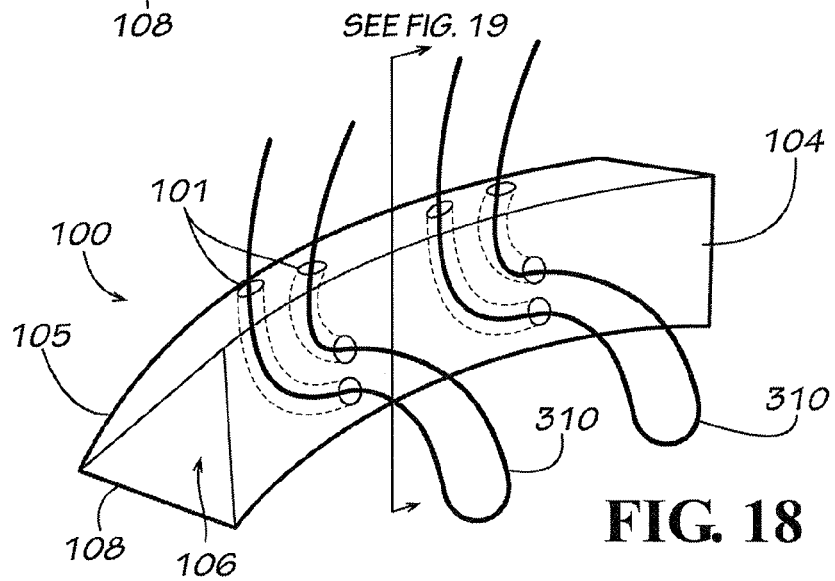
FIG. 18 is a view of the embodiment of FIG. 17 with sutures.
Figure 19:
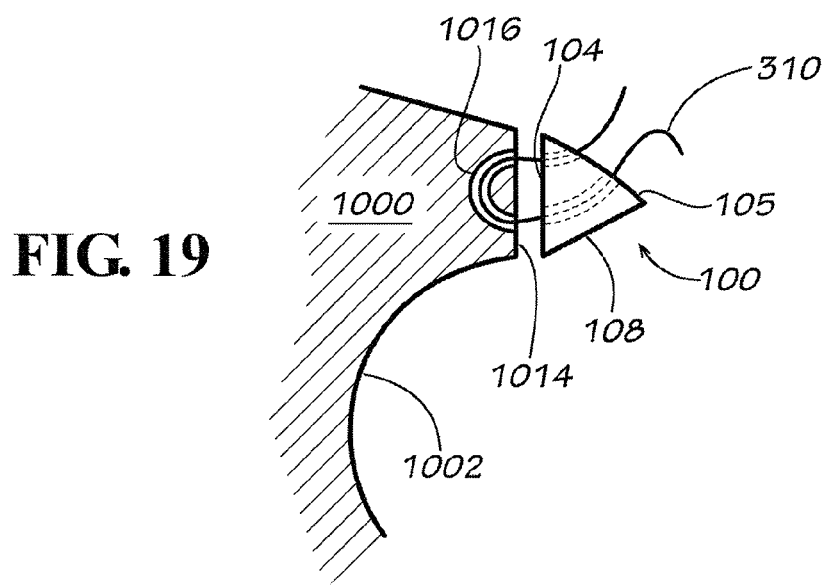
FIG. 19 is a view of the embodiment of FIG. 17 with sutures attached to an acetabulum.

FIG. 17 is a view of another embodiment of an acetabular implant 100 for treating FAI. This wedge type implant (similar to the implant of FIG. 15) may be implanted after having made a single planar cut of the acetabular rim. The implant 100 of FIG. 17, as well as FIGS. 18 and 19, may be fixed to the acetabulum with sutures or wire. FIG. 18 is a view of the embodiment of FIG. 17 with sutures 310. FIG. 19 is a view of the embodiment of FIG. 17 with sutures 310 attached to an acetabulum 1002. The sutures 310 may extend through suture guides 101 through the implant 100 and into suture guides 1016 in the bone. A bone mating surface 104, a rim portion 106, terminating in a ridge 105 extends along a bearing surface 108. Thus there is labrum replacement in a rim portion, a bearing surface transitioning to the natural cartilage in the acetabulum, and fixation means in the implant 100.

Figure 20:
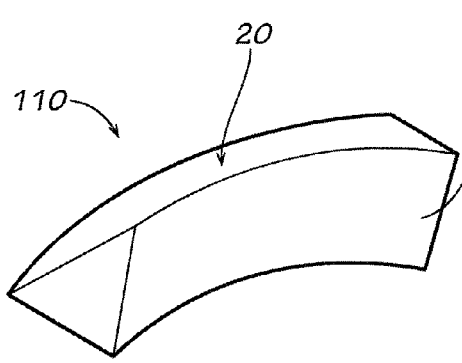
FIG. 20 is a view of another embodiment of an acetabular implant for treating FAI.
Figure 21:
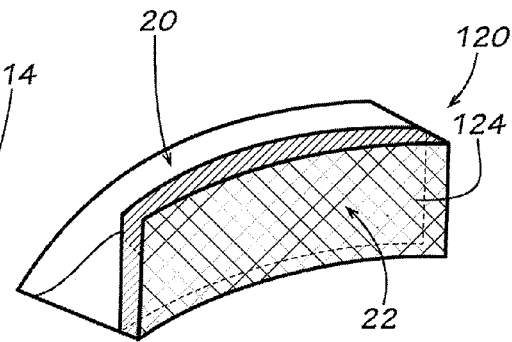
FIG. 21 is a view of another embodiment of an acetabular implant for treating FAI.
Figure 22:
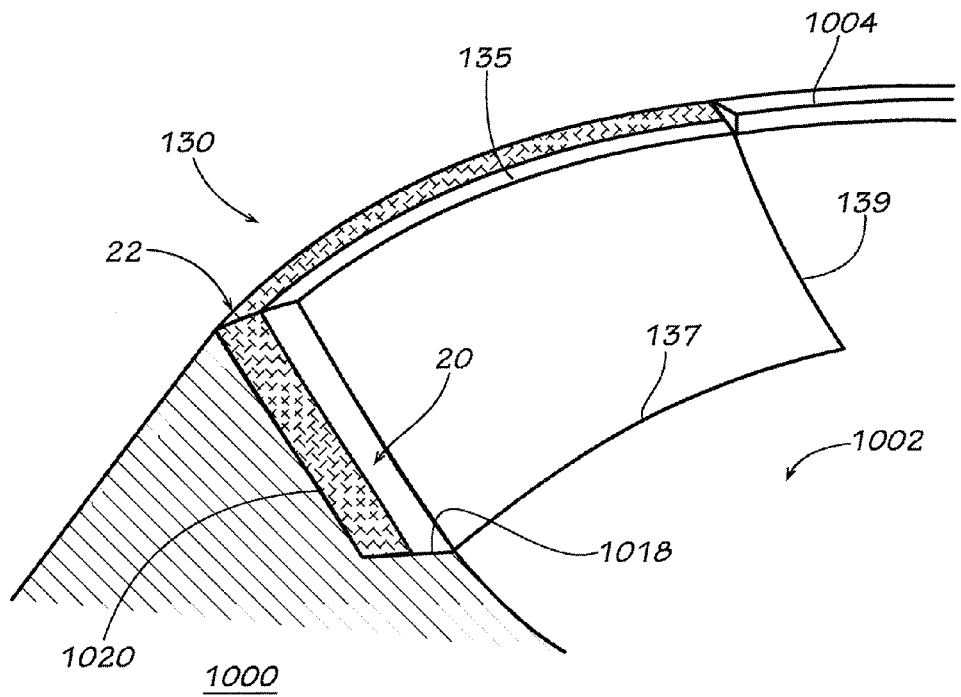
FIG. 22 is a view of another embodiment of an acetabular implant for treating FAI implanted on an acetabulum.
Figure 23:
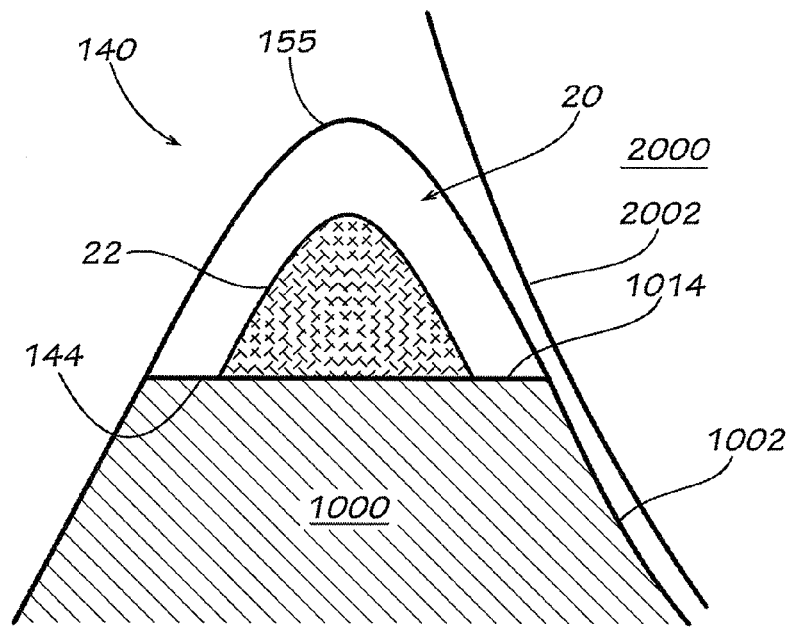
FIG. 23 is a view of another embodiment of an acetabular implant for treating FAI implanted on an acetabulum.
Figure 24:
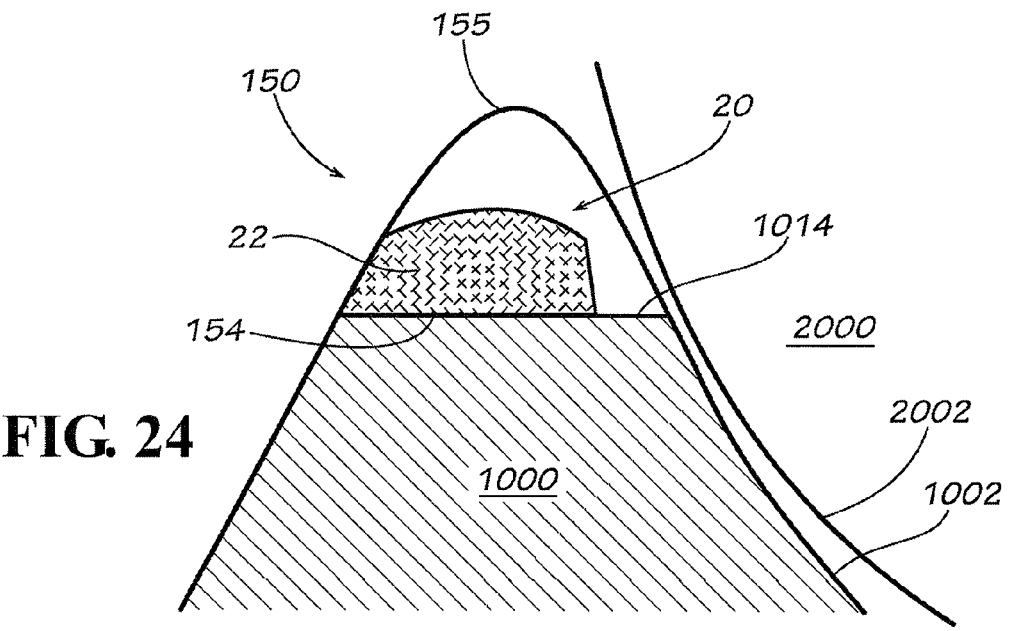
FIG. 24 is a view of another embodiment of an acetabular implant for treating FAI implanted on an acetabulum.

FIGS. 20 and 21 are views of other embodiments of an acetabular implant for treating FAI. Similar to previous embodiments, this embodiment is a wedge type design with a bi-material structure. A more rigid portion 20 and a more flexible portion 22. As previously described, such features may give the implant some compliance when implanted. As shown in FIG. 22, FIG. 22 is a view of another embodiment of an acetabular implant for treating FAI implanted on an acetabulum where the compliant material 22 is a bone interface surface. FIGS. 23 and 24 similarly show bi-material combinations where the more compliant and more rigid portions of the implant comprise different portions of the implants.

Figure 25:
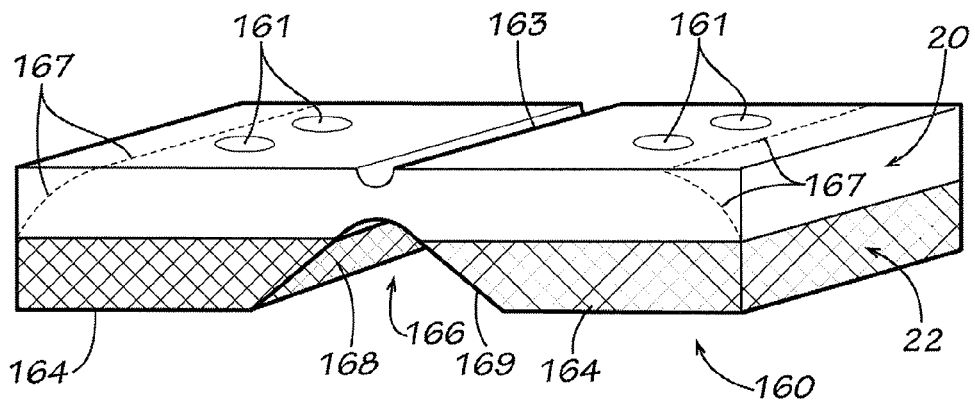
FIG. 25 is a view of another embodiment of an acetabular implant for treating FAI.

FIG. 25 is a view of another embodiment of an acetabular implant 160 for treating FAI. The implant includes more rigid material 20 and more flexible material 22. Mounting means 161 may fix the implant to the bone. A notch 166 may allow the implant to be bent. A relief 163 may be positioned opposite the notch 166 to relieve stress in the implant when it is bent. Opposing surfaces 168 and 169 may contact each other when the implant is bent. In an alternative embodiment, a chanmfer 167 may transition the bearing surface of the implant to the bone.

Figure 26:
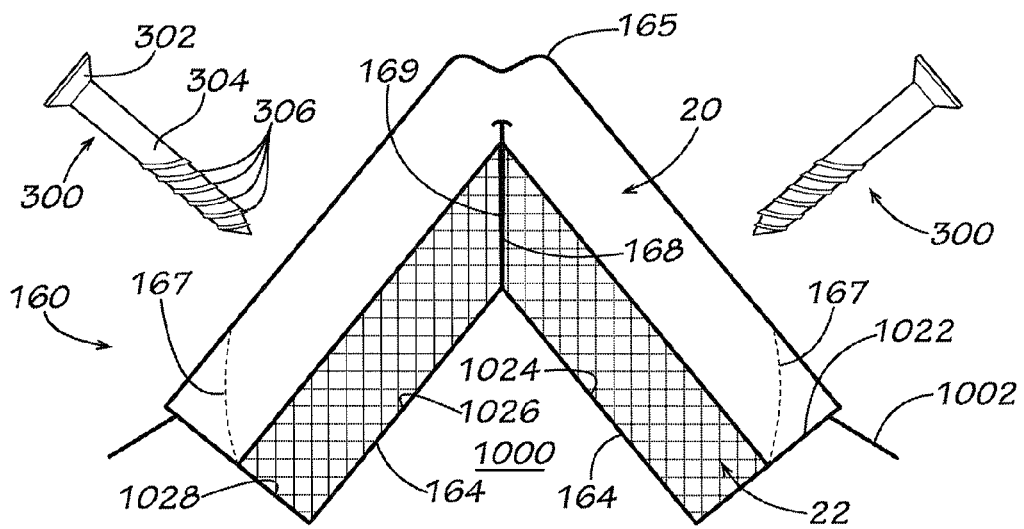
FIG. 26 is an exploded view of the implant of FIG. 25 bent into the proper shape for implantation and fixation screws.
Figure 27:
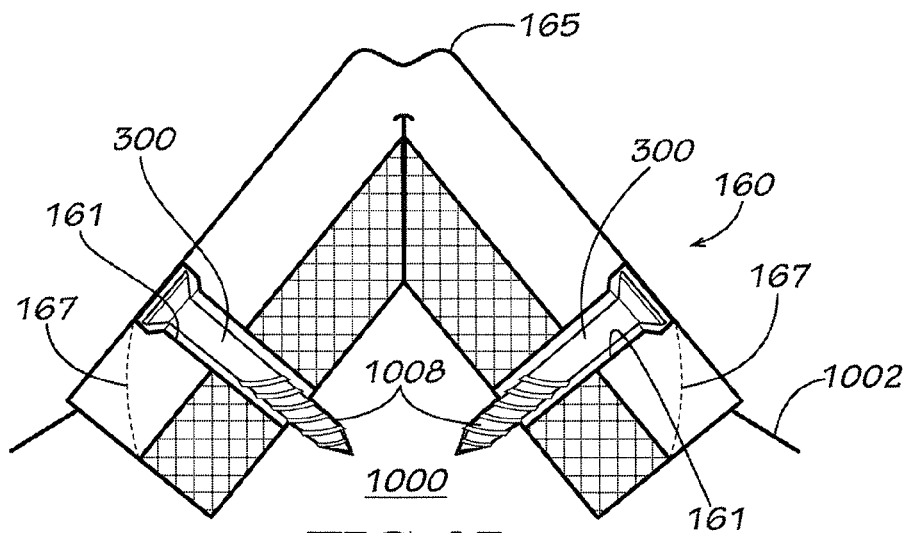
FIG. 27 is a cutaway view of the implant and screws of FIG. 26.

FIG. 26 is an exploded view of the implant of FIG. 25 bent into the proper shape for implantation and fixation screws. FIG. 27 is a cutaway view of the implant and screws of FIG. 26. The implant may form bone interfacing surfaces 1024 and 1026 to contact the bone. Screws 300 may then pass through the mounting means 161 to fix the impant 160 to the acetabulum 1002. A ridge 165 is formed when the implant is bent onto the acetabulum 1002.

Figure 28:
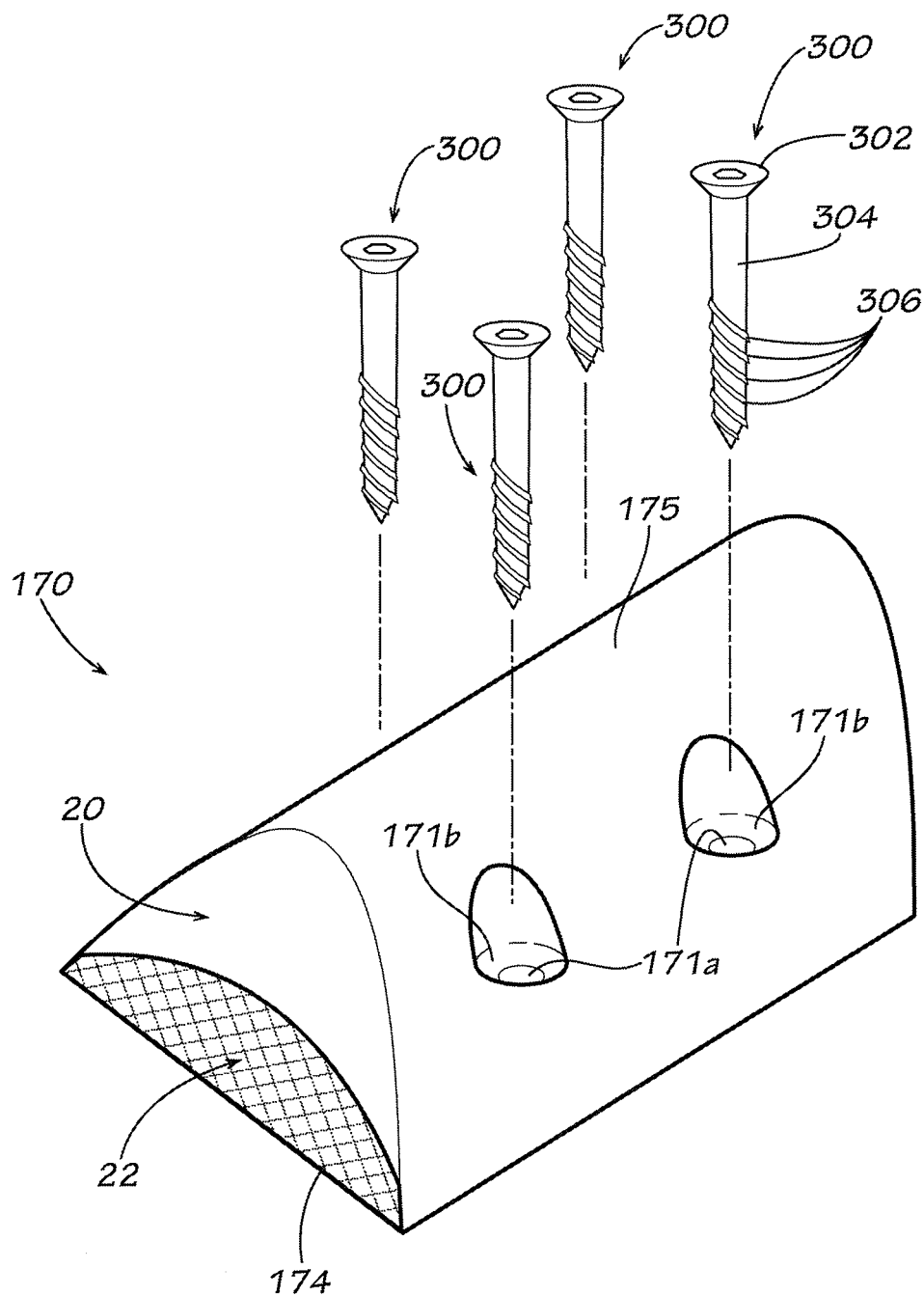
FIG. 28 is an exploded view of an embodiment of an acetabular implant and fixation screws.

FIG. 28 is an exploded view of an embodiment of an acetabular implant 170 and fixation screws 300. The implant may be made of a bi-material of more rigid material 20 and more flexible material 22. The screws 300 may be countersunk 171b with mounting holes 171a. A ridge 175 may replace the labrum when the implant is fixed to bone.

Figure 29:
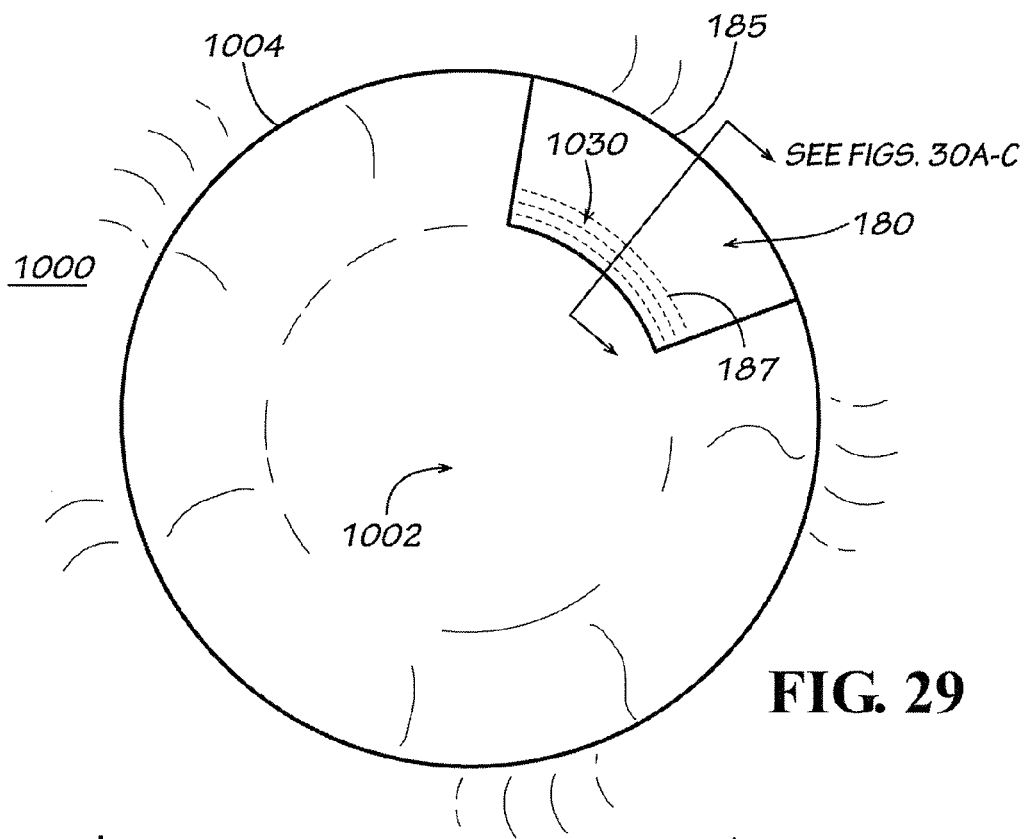
FIG. 29 is a view of an acetabulum with an implant.

FIG. 29 is a view of an acetabulum 1002 with an implant 180. The implant 180 may include a chamfer 187 between the bearing surface of the implant 180 and the articulating surface of the acetabulum. The implant may have a bone interfacing surface that runs more generally parallel to the articulating surface of the acetabulum. Two cuts that are generally perpendicular to each other form a generally rectangular recess in the bone. The load on the bone surface may be preferable in some instances with an implant design like this (as opposed to a wedge embodiment or a layover embodiment.) The general portions are still intact in such a design, namely, a bone contacting surface, a bearing surface and a constraining portion that replaces the labrum.

Figure 30A:
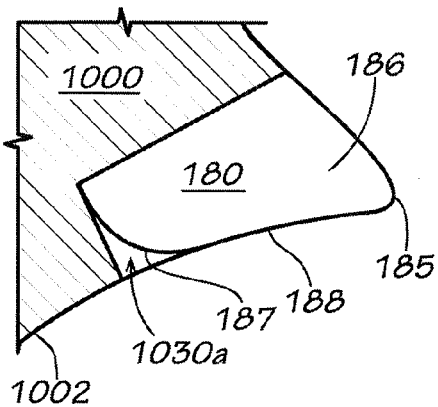
FIG. 30A is a view of an embodiment of an implant that may be implanted as shown in FIG. 29.
Figure 30B:
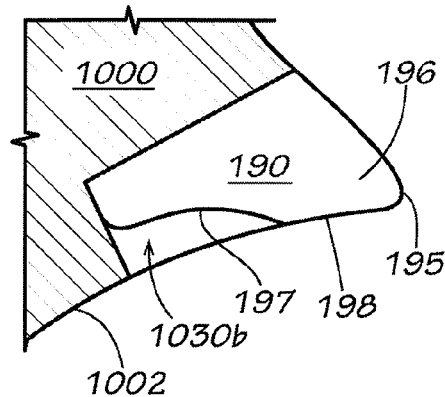
FIG. 30B is another view of an embodiment of an implant that may be implanted as shown in FIG. 29.
Figure 30C:
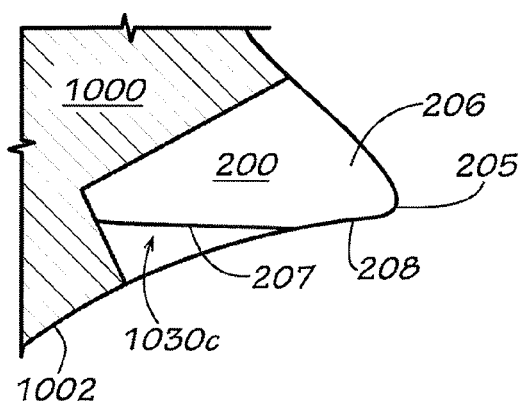
FIG. 30C is another view of an embodiment of an implant that may be implanted as shown in FIG. 29.

FIGS. 30A through 30C are views of embodiments of implants 180, 190, and 200 that may be implanted as shown in FIG. 29. In the implants a chamfer 187, 197 and 207 relieves the implant near the acetabular articulating surface and a gap 1030a, 1030b, and 1030c is formed between the implant and the acetabulum. A bearing surface 188, 198 and 208 aligns with the acetabular articulating surface. A rim portion 186, 196, and 206 extends into the acetabular cavity and terminates in a ridge 185, 195 and 205 that replaces the labrum.

Figure 31:
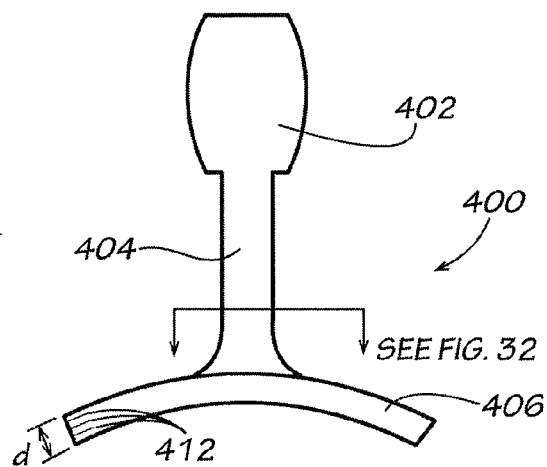
FIG. 31 is a view of a guide marker for an acetabular implant.
Figure 32:
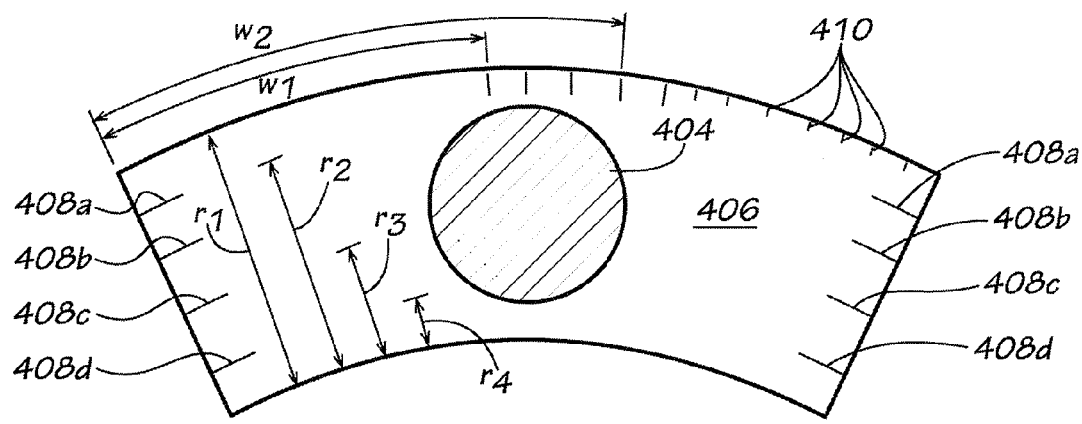
FIG. 32 is another view of the guide marker of FIG. 31.

FIG. 31 is a view of a guide marker 400 for an acetabular implant. A handle 402 extends along a shaft 404 to a guide 406. Depth indicia 412 on the guide 406 may set the depth of the implant while radii (r1, r2, r3, and r4) by markings 408a-d (shown in FIG. 32). Widths (w1, w2) may be determined through markings 410. Based upon the necessary bone removal, the markings may determine the size of the implant, the depth to which the bone must be removed in order for the implant to fit properly, and the correct radius of the implant.

Figure 33:
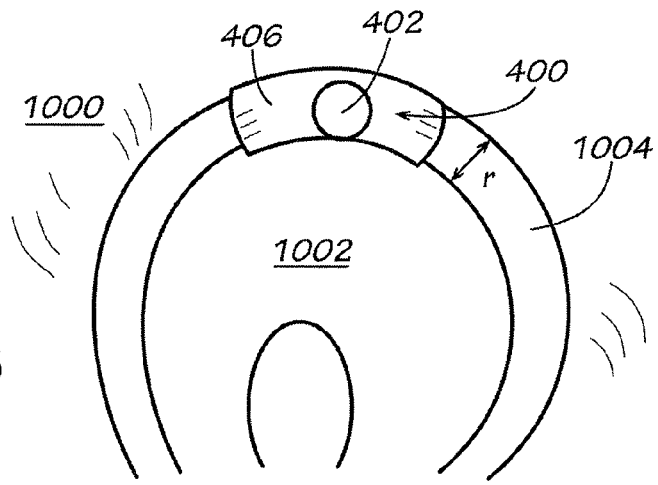
FIG. 33 is a view of the guide marker of FIG. 31 placed on the surface of an acetabulum.

FIG. 33 is a view of the guide marker of FIG. 31 placed on the surface of an acetabulum. The guide uses the radius markings to make sure the proper radius of the acetabulum is determined. By aligning an edge of the guide on one end of the damaged site, the width markings may be used to measure the width of the implant. The depth may be determined from the markings 112 which may show the depth of removal necessary for the implant to sit flush with the articulating surface of the acetabulum.

Figure 34:
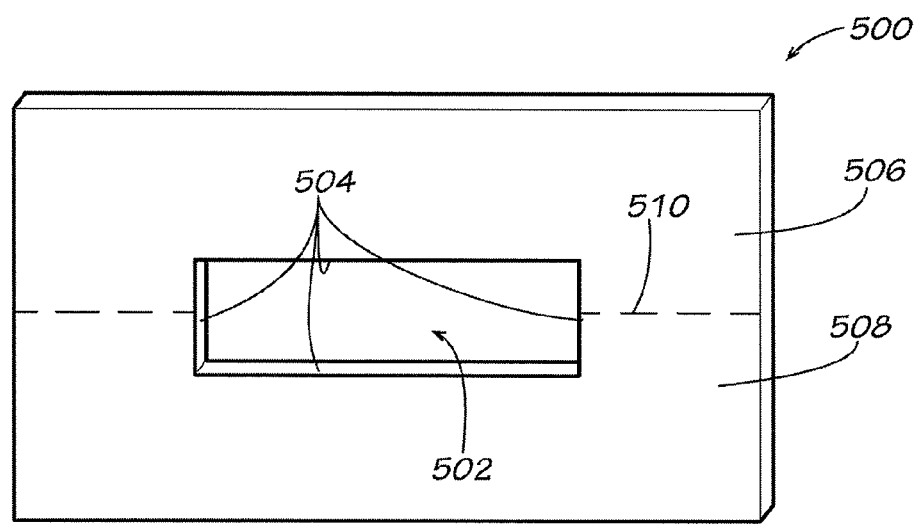
FIG. 34 is a view of a bone cutting guide.
Figure 35:
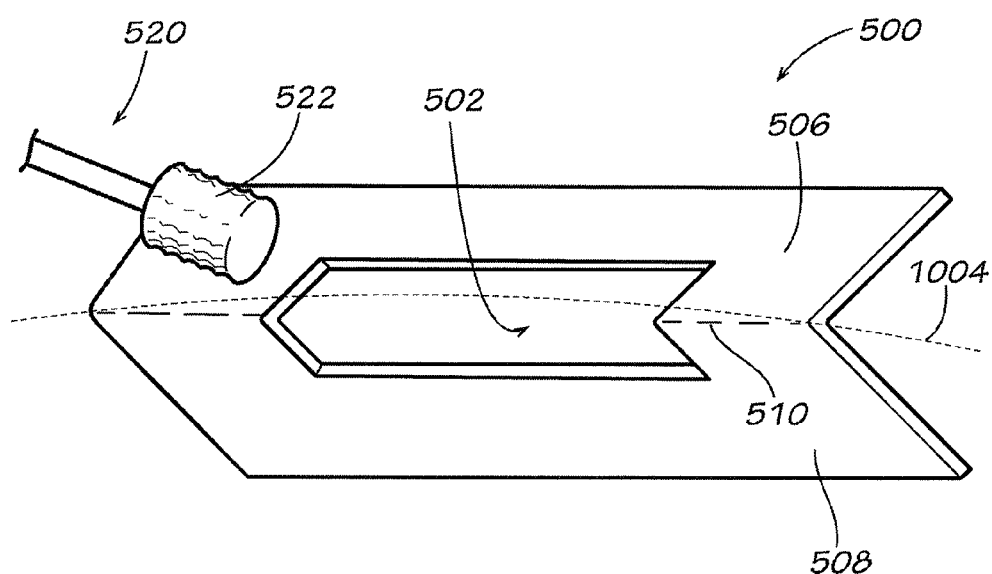
FIG. 35 is a view of a cutter and the bone cutting guide of FIG. 34 folded into a proper orientation to be received on an acetabulum.

FIG. 34 is a view of a bone cutting guide 500. An opening 502 in the guide 500 creates guide surfaces 504 for the depth of cutting. The guide 500 may be bent so that a lower portion 508 and an upper portion 506 overlie the rim of the acetabulum. As shown in FIG. 35, FIG. 35 is a view of a cutter 522 on a surgical tool 520 and the bone cutting guide of FIG. 34 folded into a proper orientation to be received on an acetabulum.

Figure 36:
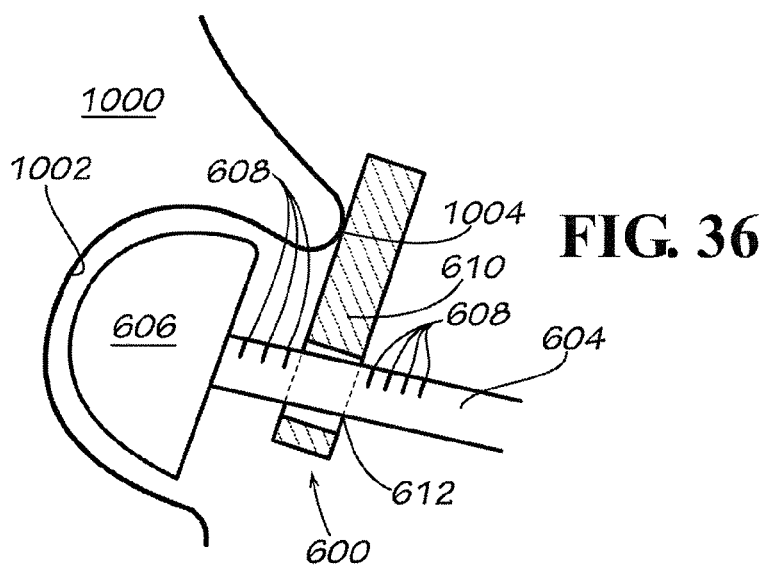
FIG. 36 is a view of a measuring instrument oriented in the acetabulum.
Figure 37:
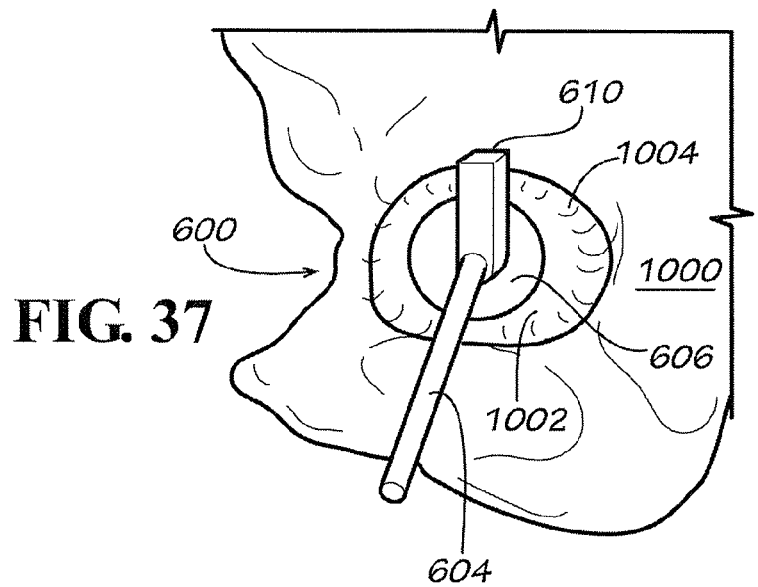
FIG. 37 is another view of the measuring instrument of FIG. 36 oriented in the acetabulum.

FIG. 36 is a view of a measuring instrument 600 oriented in the acetabulum 1002. The instrument 600 includes a shaft 604 attached to a hemispherical head 606. Depth marks 608 are located on the shaft 604. A stylus 610 slides along the shaft 604 in a shaft guide 612. The head 606 may be positioned within the acetabulum to orient the version and adduction of the shaft. The stylus may then measure the depth to the lesion 1004 by using the markings 608. Radius markings on the stylus may measure the radius of the acetabular rim. FIG. 37 is another view of the measuring instrument of FIG. 36 oriented in the acetabulum.

Figure 38:
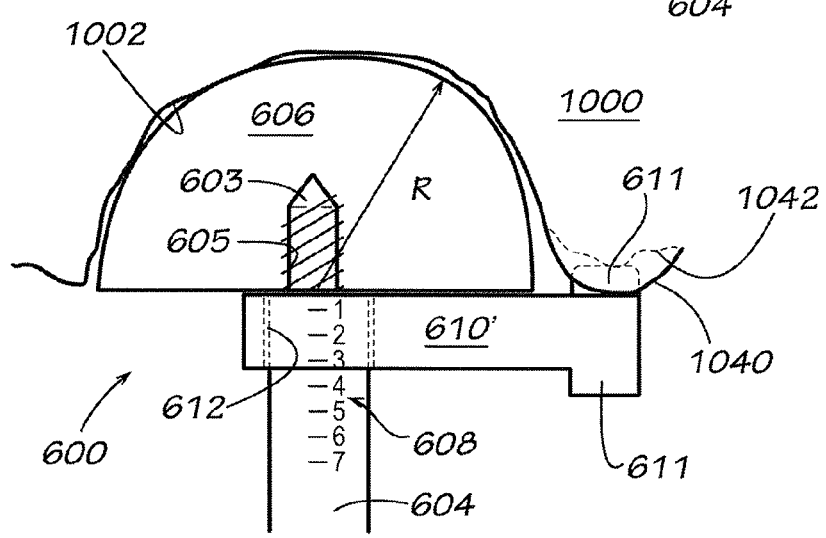
FIG. 38 is a view of another embodiment of a measuring instrument.

FIG. 38 is a view of another embodiment of a measuring instrument 600. The stylus 610' may be reversible. Additionally a lesion depth paddle 611 may be placed on the end of the stylus. The stylus 610' may measure the depth from the shaft, and the paddle 611 may measure the depth of the lesion.

Figure 39:
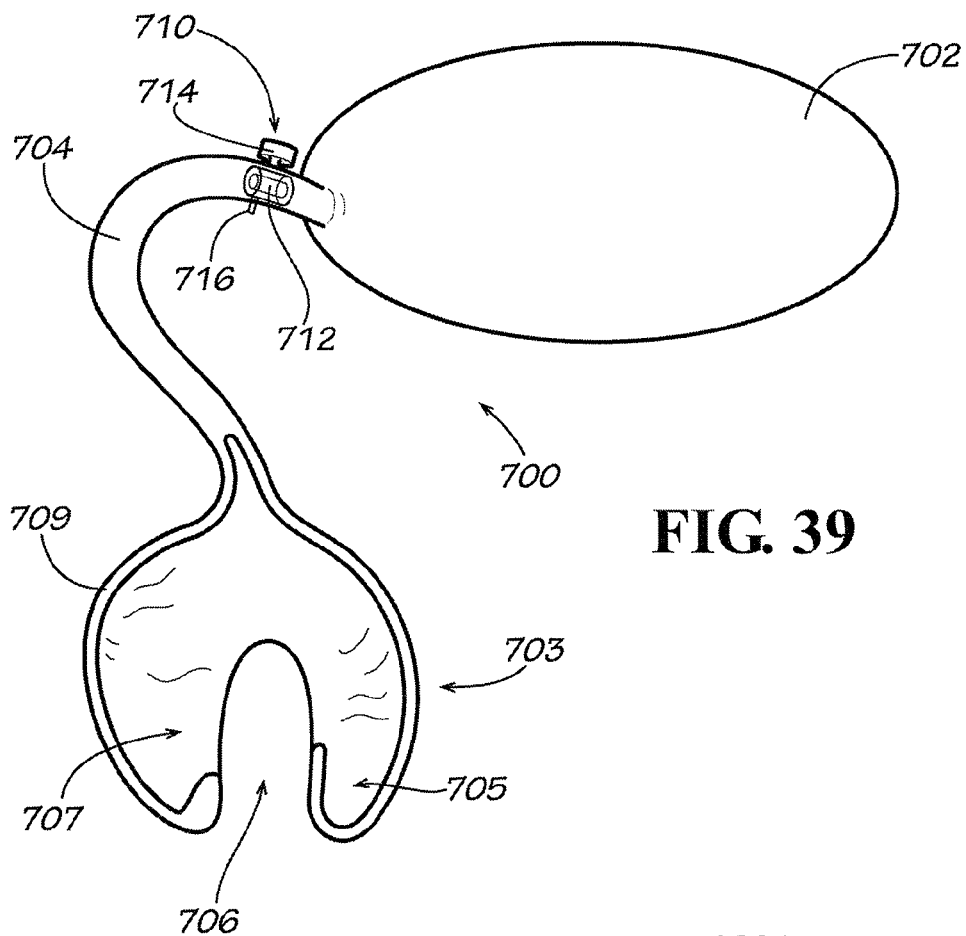
FIG. 39 is a view of a spacer instrument for separating the femur from the acetabulum.
Figure 40:
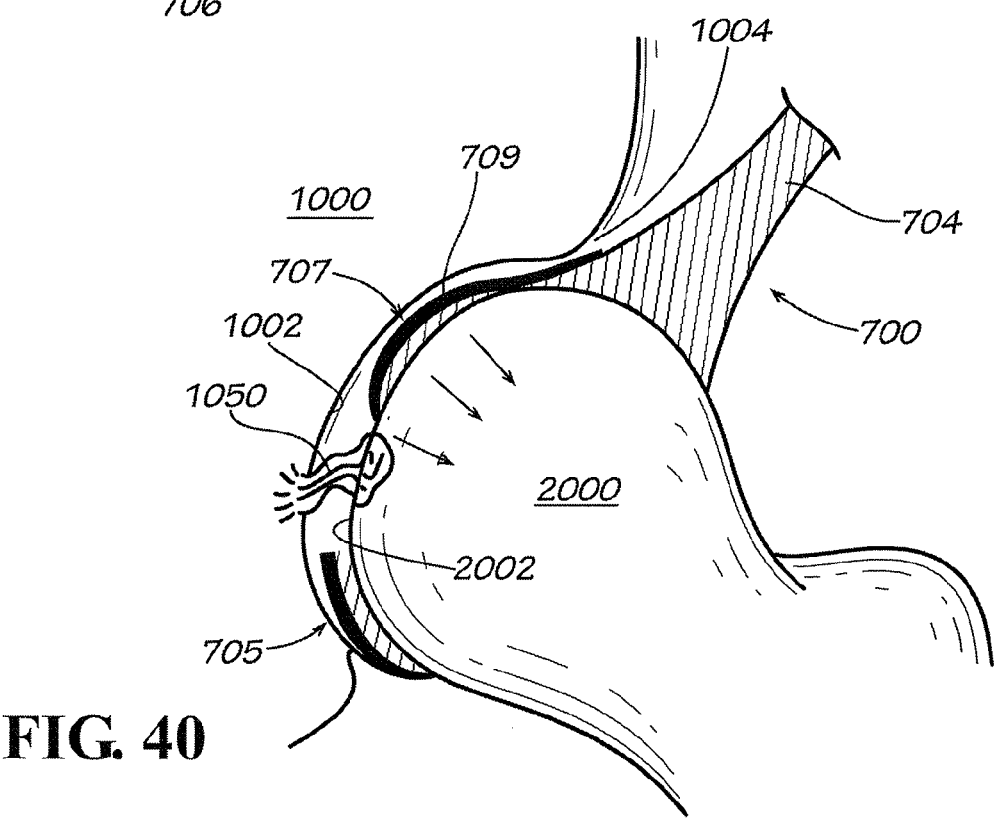
FIG. 40 is a partial view of the spacer instrument of FIG. 39 inserted into the hip joint around the ligamentum teres.

FIG. 39 is a view of a spacer instrument 700 for separating the femur from the acetabulum. The spacer instrument 700 includes a plenum 702 attached to a forked inflatable spoon 703 through a tube 704. The spoon 703 includes a first finger 705 and a second finger 707 separated by a cutout portion 706. A stiffening member 709 may stiffen the spoon 703 for insertion. A control module 710 includes a one way valve 712, a pressure release knob 714 and a pop-off valve 716. The plenum 702 may inflate the spoon 703 to inflate the finger portions 705 and 707. The finger portions 705 and 707 (as shown in FIG. 40) may avoid the ligamentum teres. When inflated, the spoon may separate the femur from the acetabulum without tearing the ligamentum teres. Stiffening means 709 may be placed along the edge of the spoon 703 so that the spoon may be pushed into the hip joint.

FIG. 41 is a view of an acetabulum showing pathways 1060 from the iliac crest to labral or acetabular defects. FIG. 42 is another view of the acetabulum of FIG. 41 showing pathways from the iliac crest to labral or acetabular defects. The pathways 1060 allow for distal to proximal orientation of an implant or a proximal to distal orientation of an implant. By using these different pathways through the iliac crest, the implant orientation at the labrum may be controlled. The implants inserted through these pathways are shown in FIGS. 43A to 43F.

FIGS. 43A to 43F are views of different embodiments of acetabular implants to insert into the pathways shown in FIG. 41 and FIG. 42. Each implant 210, 220, 230, 240, 250, and 260 have a post that extends along the pathway. Each implant has a ridge (like 215 in 43A), a bearing portion (e.g., 228 in FIG. 43B), and a rim portion (like 236 in FIG. 43C). The posts may be made of a compliant material 22, press fit into an implant, or threaded. Threaded designs may have rotational members 242 or 252 depending on proximal or distal direction of the implantation. The posts provide fixation for the implant in the bone 1000.

Figure 44:
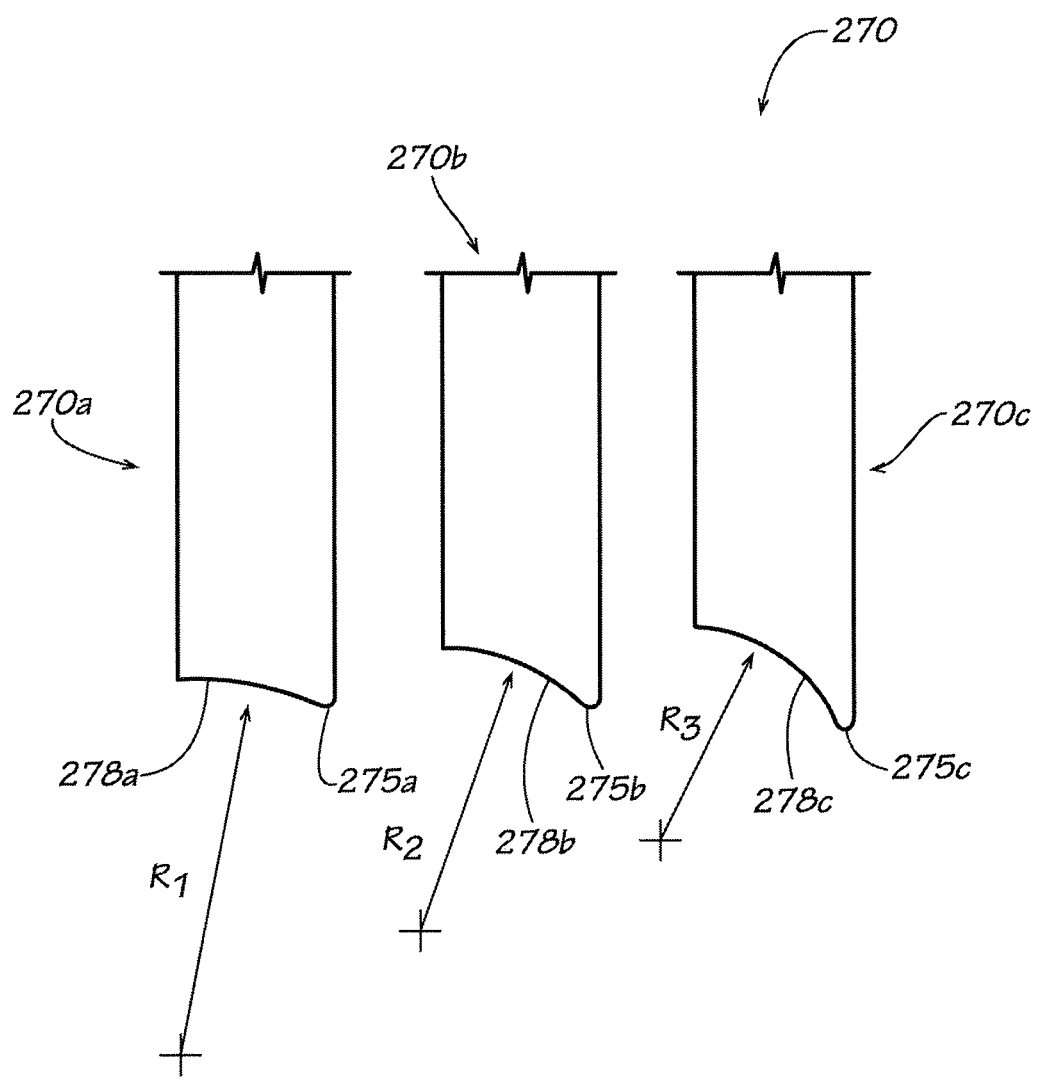
FIG. 44 is a view of a plurality of bone mating surfaces of acetabular implants having various radii.

FIG. 44 is a view of a plurality of bone mating surfaces 278a, 278b, and 278c of acetabular implants having various radii R1, R2, R3. With the varying radii and the varying directions, as well as the ability to control the depth of the implants in the bone, the proper orientation may be accomplished with good fixation, proper bearing placement and proper labrum replacement.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A partial rim implant for an acetabulum in a pelvic bone, wherein the acetabulum comprises an articulating surface, a rim, and an apex, the implant comprising:
 a. a ridge oriented to replace a labrum;
 b. a bearing surface configured to align with the articulating surface of the acetabulum, wherein the bearing surface extends from the ridge toward the apex of the acetabulum;
 c. an insertion portion extending at an angle away from the bearing surface, wherein the insertion portion is adapted to engage a bone recess in the pelvic bone; and
 d. at least one flange portion extending from the ridge and away from the bearing surface; and
 wherein the bearing surface extends between the ridge and the insertion portion; and wherein the insertion portion and the at least one flange portion are angled toward one another as the insertion portion and the at least one flange portion extend away from the bearing surface.

2. The implant of claim 1, wherein the implant is fixed to the acetabulum with sutures.

3. The implant of claim 1, wherein the insertion portion and the flange portion each extend away from the bearing surface in the same general direction and define a space therebetween sized and configured for receipt of a portion of the pelvic bone therein.

4. The implant of claim 3, wherein the at least one flange portion comprises at least one screw hole.

5. The implant of claim 3, wherein the at least one flange portion comprises at least two fixation flanges.

6. The implant of claim 1, further comprising a substantially planar fixation surface adapted to adjoin a substantially planar prepared surface of the acetabulum.

7. The implant of claim 6, wherein the flange portion the substantially planar fixation surface and a screw hole.

8. The implant of claim 7, further comprising a rim portion defining the ridge and the bearing surface.

9. The implant of claim 1, wherein the bearing surface is curved between the ridge and the insertion portion.

10. The implant of claim 9, wherein the bearing surface comprises a concave curvature extending between the ridge and the insertion portion.

11. The implant of claim 1, wherein the at least one flange portion comprises at least one fastener opening.

12. The implant of claim 1, wherein the implant comprises a first material and a different second material each having a rigidity, wherein the rigidity of the first material is greater than the rigidity of the second material.

13. The implant of claim 12, wherein at least a portion of the bearing surface comprises the first material and at least one of the insertion portion and the flange portion comprises the second material.

14. The implant of claim 13, wherein the insertion portion and the flange portion each comprise the second material.

15. The implant of claim 12, wherein the first material comprises a metallic material and the second material comprises a polymeric material.

16. The implant of claim 12, wherein the second material comprises a polymeric material.

17. A partial rim implant for an acetabulum in a pelvic bone, wherein the acetabulum comprises an articulating surface, a rim, and an apex, the implant comprising:
 a. a ridge oriented to replace a labrum; and
 b. a bearing surface configured to align with the articulating surface of the acetabulum, wherein the bearing surface extends from the ridge toward the apex of the acetabulum;
 c. an insertion portion extending at an angle away from the bearing surface, wherein the insertion portion is adapted to engage a bone recess in the pelvic bone; and
 d. at least one flange portion extending from the ridge and away from the bearing surface; and
 wherein the at least one flange portion comprises at least one screw hole; and
 wherein the insertion portion and the at least one flange portion are angled toward one another as the insertion portion and the at least one flange portion extend away from the bearing surface.

18. The implant of claim 17, wherein the at least one flange portion is adapted to lie substantially flush with a portion of the pelvic bone.

19. The implant of claim 17, wherein the bearing surface comprises a concave curvature extending between the ridge and the insertion portion.

20. The implant of claim 17, wherein the insertion portion and the flange portion each extend away from the bearing surface in the same general direction and define a space therebetween sized and configured for receipt of a portion of the pelvic bone therein.

21. A partial rim implant for an acetabulum in a pelvic bone, wherein the acetabulum comprises an articulating surface, a rim, and an apex, the implant comprising:
 a. a ridge oriented to replace a labrum;
 b. a bearing surface configured to align with the articulating surface of the acetabulum, wherein the bearing surface extends from the ridge toward the apex of the acetabulum;
 c. an insertion portion extending at an angle away from the bearing surface, wherein the insertion portion is adapted to engage a bone recess in the pelvic bone; and
 d. at least one flange portion extending from the ridge and away from the bearing surface; and
 wherein the insertion portion and the at least one flange portion converge toward one another as the insertion portion and the at least one flange portion extend away from the bearing surface.

22. The implant of claim 21, wherein the implant is rolled onto the rim of the acetabulum.

23. The implant of claim 21, wherein the bearing surface comprises a concave curvature extending between the ridge and the insertion portion.

24. The implant of claim 21, wherein the insertion portion and the flange portion each extend away from the bearing surface in the same general direction and define a space therebetween sized and configured for receipt of a portion of the pelvic bone therein.

25. The implant of claim 21, wherein the implant comprises a first material and a different second material each having a rigidity, wherein the rigidity of the first material is greater than the rigidity of the second material; and
 wherein at least a portion of the bearing surface comprises the first material and at least one of the insertion portion and the flange portion comprises the second material.

26. The implant of claim 25, wherein the first material comprises a metallic material and the second material comprises a polymeric material.

27. A partial rim implant for an acetabulum in a pelvic bone, wherein the acetabulum comprises an articulating surface, a rim, and an apex, the implant comprising:
 a. a ridge oriented to replace a labrum;
 b. a bearing surface configured to align with the articulating surface of the acetabulum wherein the bearing surface extends from the ridge toward the apex of the acetabulum;
 c. an insertion portion extending at an angle away from the bearing surface, wherein the insertion portion is adapted to engage a bone recess in the pelvic bone; and
 d. at least one flange portion extending from the ridge and away from the bearing surface; and
 wherein the implant comprises a first material and a second material each having a rigidity, wherein the rigidity of the first material is greater than the rigidity of the second material; and
 wherein at least a portion of the bearing surface comprises the first material and at least one of the insertion portion and the flange portion comprises the second material.

28. The implant of claim 27, wherein the ridge of the implant comprises the second material.

29. The implant of claim 27, wherein the ridge of the implant comprises the first material.

30. The implant of claim 27, wherein the insertion portion and the flange portion each comprise the second material.

31. The implant of claim 27, wherein the second material comprises a polymeric material.

32. The implant of claim 27, wherein the first material comprises a metallic material and the second material comprises a polymeric material.

33. The implant of claim 27, wherein the insertion portion and the at least one flange portion are angled toward one another as the insertion portion and the at least one flange portion extend away from the bearing surface.

* * * * *